(12) United States Patent
Makino et al.

(10) Patent No.: US 8,084,248 B2
(45) Date of Patent: Dec. 27, 2011

(54) REVERSE GENETIC SYSTEM FOR RIFT VALLEY FEVER VIRUS AND USES THEREOF

(75) Inventors: Shinji Makino, Galveston, TX (US); Tetsuro Ikegami, Galveston, TX (US); Clarence J. Peters, Galveston, TX (US); Sungyong Won, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 40 days.

(21) Appl. No.: 11/606,700

(22) Filed: Nov. 30, 2006

(65) Prior Publication Data

US 2007/0122431 A1 May 31, 2007

Related U.S. Application Data

(60) Provisional application No. 60/740,853, filed on Nov. 30, 2005.

(51) Int. Cl.
*C12N 15/00* (2006.01)
*C12N 15/11* (2006.01)

(52) U.S. Cl. .................................. 435/320.1; 435/169.1

(58) Field of Classification Search ................ 435/320.1
See application file for complete search history.

(56) References Cited

OTHER PUBLICATIONS

Simons et al. J. Virol. 1990, vol. 64, No. 1, pp. 247-255.*
Accardi et al. J. Gene. Virol. 2001, vol. 82, pp. 781-785.*
Ikegami et al. J. Virol. May 2005, vol. 79, No. 9, pp. 5606-5615.*
Lowen et al. Virology 2004, Dec. 20, vol. 330 (2), pp. 493-500.*
Ikegami et al.(B) Virus, Dec. 2004, vol. 54, No. 2, pp. 229-236.*
Walpita et al. FEMS Microbiology Letter 2005, vol. 244, pp. 9-18.*
Medical Dictionary on line, pp. 1-4, searched on Jul. 16, 2009.*
MedicineNote.com, pp. 1-2, searched on Jul. 16, 2009.*

* cited by examiner

*Primary Examiner* — Bao Li

(57) ABSTRACT

The present invention describes a reverse genetic system for *Phlebovirus* such as Rift Valley fever virus. This system comprised of RNA expression plasmids and protein expression plasmids. Additionally, the present invention also discloses the modification of this system to generate a recombinant virus that expresses a non-viral foreign gene. Furthermore, the present invention discloses the use of this system in the development of anti-Rift Valley fever virus vaccines, screening of antivirals testing for anti RVF immune response and developing marker vaccines for Rift Valley fever virus. We also claim the utility of this approach to other *phleboviruses*.

10 Claims, 14 Drawing Sheets

419
Silent mutation

```
               5'         ↓            3'
MP-12 Sv    CTAAGCTCTACTAGAGTGCATAGG    SEQ ID NO: 1
rMP-12 Sv   CTAAGCTCTACTCGAGTGCATAGG    SEQ ID NO: 2
                       XhoI
a.a.(NSs)      L   S   S   T   R   V   H   R    SEQ ID NO: 3
```

3478 3480
Silent mutation

```
               5'        ↓↓             3'
MP-12 Mvc   ATAGATCAATTGGAGTGCACAACA    SEQ ID NO: 4
rMP-12 Mvc  ATAGATCAACTCGAGTGCACAACA    SEQ ID NO: 5
                       XhoI
a.a.(G1)       I   D   Q   L   E   C   T   T    SEQ ID NO: 6
```

3814 3816
Silent mutation

```
               5'        ↓↓             3'
MP-12 Lvc   GAGCTATTCTTAGAGTATAAGAAG    SEQ ID NO: 7
rMP-12 Lvc  GAGCTATTCCTCGAGTATAAGAAG    SEQ ID NO: 8
                       XhoI
a.a.(L)        E   L   F   L   E   Y   K   K    SEQ ID NO: 9
```

Fig. 1A

```
nt          5'                          79        629              3'
C13              UUGCAGAGUGGUCGU           CACGCAGCAAA
                 SEQ ID NO: 10             SEQ ID NO: 11
rMP-12-C13type  UUGCAGAGUGGUCGU GACGUC CACGCAGCAAA
                      SEQ ID NO: 14 a.a.        N-term                                    C-term
C13            L Q S G R                    Q   A A K
               SEQ ID NO:12                 SEQ ID NO:13
rMP-12-C13type L Q S G R  D V  Q  A A K
                      SEQ ID NO: 15 nt          5'          28               820              3'
MP-12            UAUCAAGUAUAUCAGU....... UGAGGUUGAUUAG
                 SEQ ID NO: 16           SEQ ID NO: 17
rMP-12NSdel  UAUCAAG  GUUCUAGUUGAGGUUGAUUAG
                        SEQ ID NO: 18 a.a.        N-term                                    C-term
MP-12                       M  .........    E V D    Stop
rMP-12NSdel  -- ------------------------------------------
```

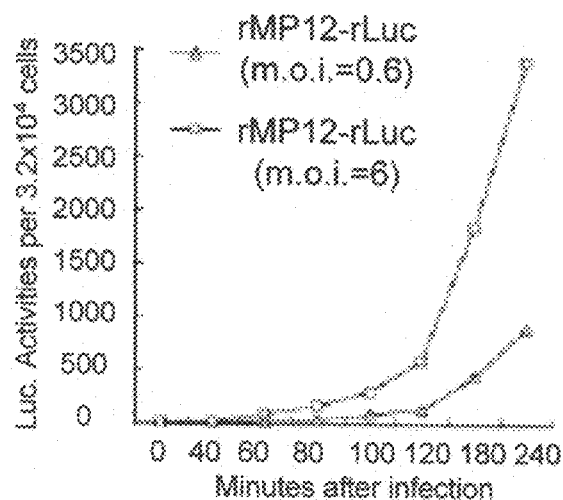
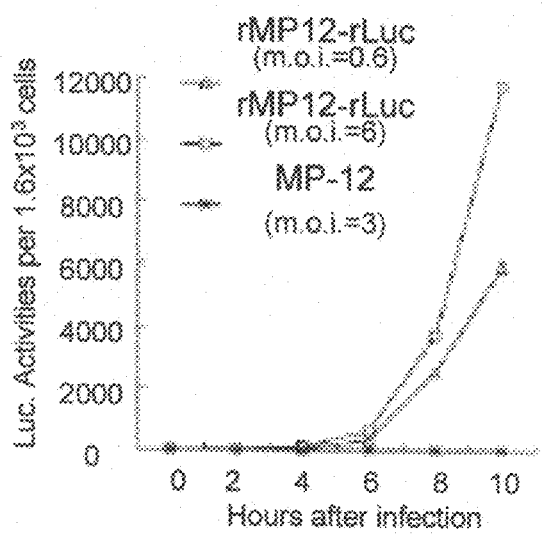
Fig. 3B
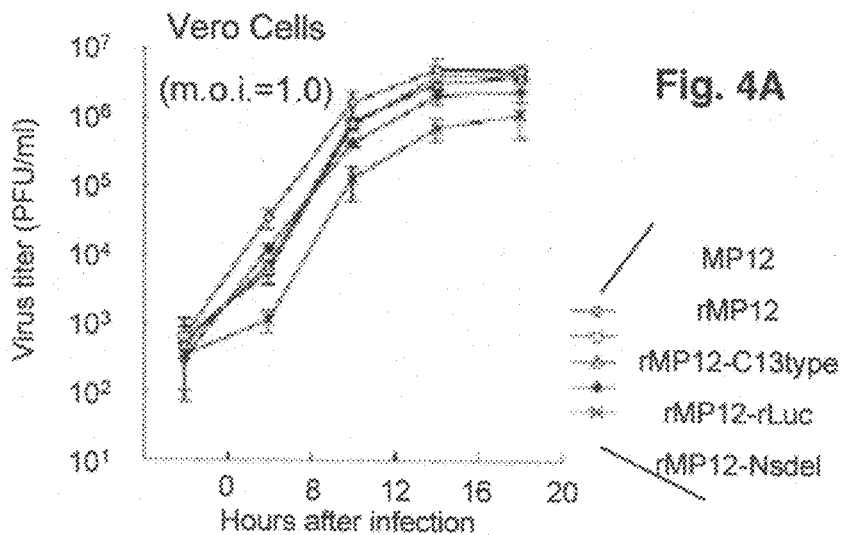
Fig. 4A

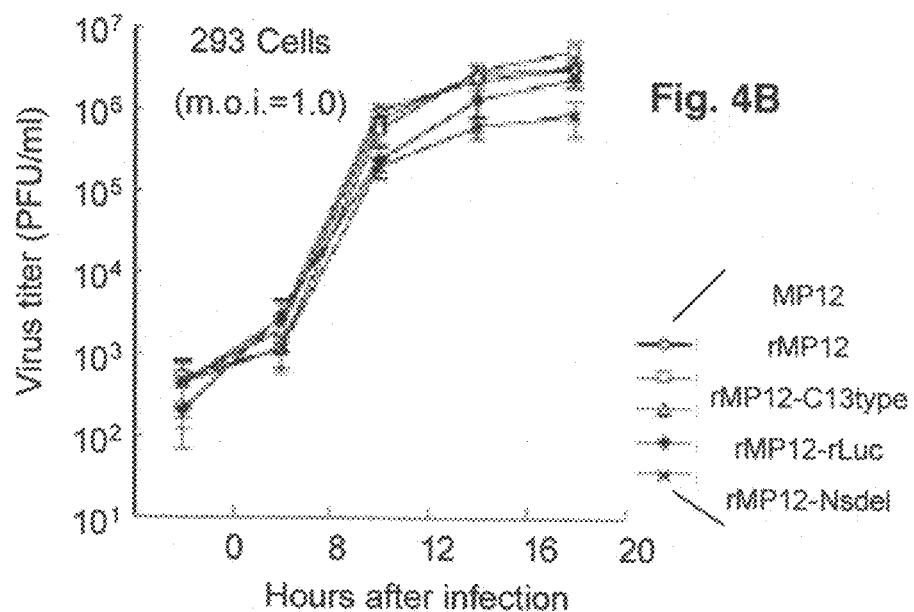
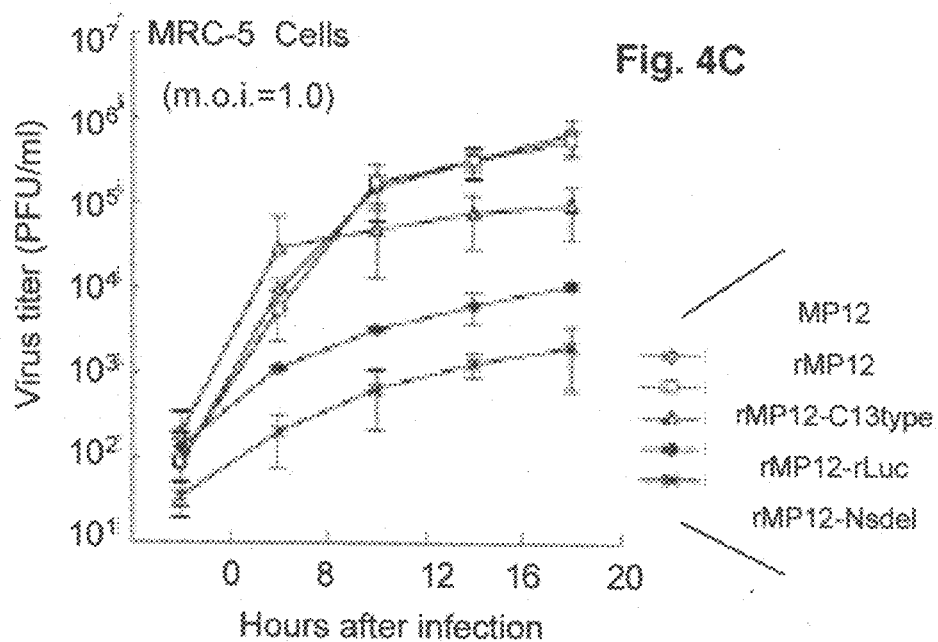

Fig. 5

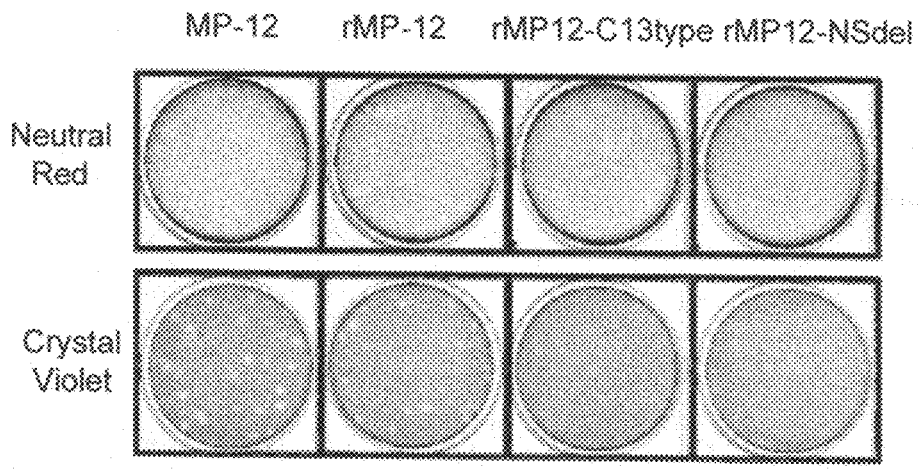
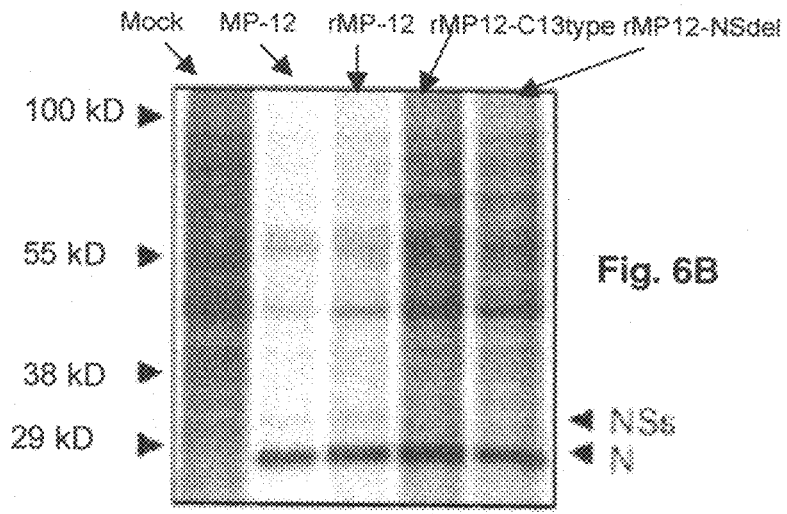
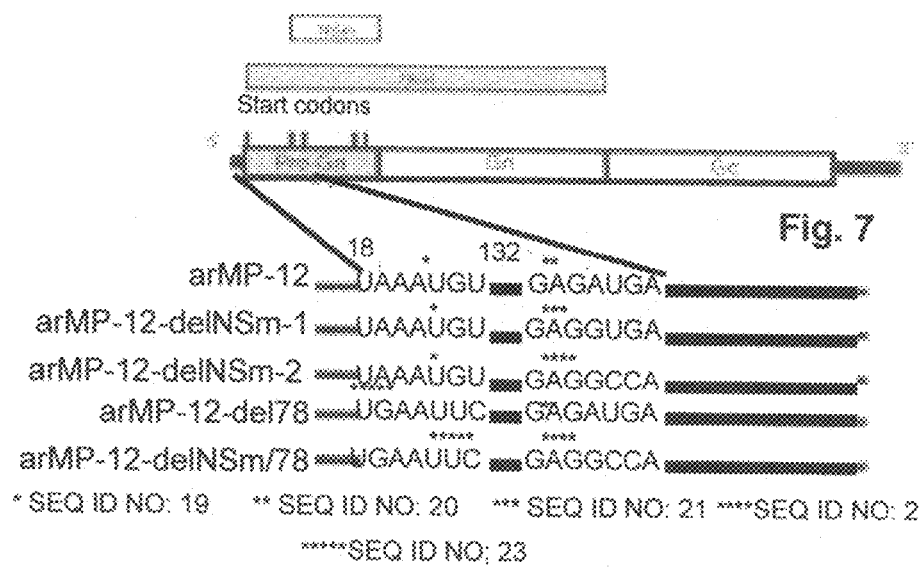
Fig. 7
* SEQ ID NO: 19   SEQ ID NO: 20  * SEQ ID NO: 21  ****SEQ ID NO: 22
***** SEQ ID NO: 23

Fig. 8D 78-kDa →
Gn/Gc →

N →

IP: Anti-RVFV antibody    Preimmune

Lanes: Mock, MP-12, rMP-12, rMP-12-delNSs, rMP-12-del21/384, MP-12

Fig. 11 rMP-12 infection          rMP-12-del21/384 infection

Boxes represent IL-6 signals       Fig. 12

Fig. 13

Cells, MRC-5 cells; RNA extraction, 8 h p.i.

Lvc, antiviral-sense L RNA; Mvc, antiviral-sense M RNA; Svc, antiviral-sense S RNA; Lv, viral-sense L RNA; Mv, Viral-sense M RNA; Sv, viral-sense S RNA; N, N mRNA

Fig. 14

Cells: MRC-5 cells; extraction, 8h p.i.
A: anti-RVFV antibody
B: anti-NSs antibody
C: anti-RVFV antibody
D: anti-Gn monoclonal antibody
E: anti-alpha-actin antibody

SEQUENCE LISTING

<160> NUMBER OF SEQ ID NOS: 25

<210> SEQ ID NO 1
<211> LENGTH: 24
<212> TYPE: DNA
<213> ORGANISM: Artificial Sequence
<220> FEATURE:
<223> OTHER INFORMATION: nucleotide sequence for virus-sense S gene
      segment MP-12Sv of Rift Valley Fever Virus
      (RVFV) strain rMP-12

<400> SEQUENCE: 1
ctaagctcta ctagagtgca tagg                                              24

<210> SEQ ID NO 2
<211> LENGTH: 24
<212> TYPE: DNA
<213> ORGANISM: Artificial Sequence
<220> FEATURE:
<223> OTHER INFORMATION: nucleotide sequence for virus-sense S gene
      segment rMP-12Sv of recombinant RVFV strain rMP-12

<400> SEQUENCE: 2
ctaagctcta ctcgagtgca tagg                                              24

<210> SEQ ID NO 3
<211> LENGTH: 8
<212> TYPE: PRT
<213> ORGANISM: Artificial Sequence
<220> FEATURE:
<221> NAME/KEY: CHAIN
<223> OTHER INFORMATION: amino acid sequence within a Nss protein of
      RVFV strain MP-12

<400> SEQUENCE: 3

Leu Ser Ser Thr Arg Val His Arg
                5

<210> SEQ ID NO 4
<211> LENGTH: 24
<212> TYPE: DNA
<213> ORGANISM: Artificial Sequence
<220> FEATURE:
<223> OTHER INFORMATION: nucleotide sequence for anti-viral sense M gene
      segment MP-12Mvc of RVFV strain MP-12

<400> SEQUENCE: 4
atagatcaat tggagtgcac aaca                                              24

<210> SEQ ID NO 5
<211> LENGTH: 24
<212> TYPE: DNA
<213> ORGANISM: Artificial Sequence
<220> FEATURE:
<223> OTHER INFORMATION: nucleotide sequence for anti-viral M gene
      segment MP-12Mvc of recombinant RVFV strain rMP-12

<400> SEQUENCE: 5
atagatcaac tcgagtgcac aaca                                              24

<210> SEQ ID NO 6
<211> LENGTH: 8
<212> TYPE: PRT
<213> ORGANISM: Artificial Sequence
<220> FEATURE:
<221> NAME/KEY: CHAIN
<223> OTHER INFORMATION: amino acid sequence within a G1 protein of RVFV strain MP-12

<400> SEQUENCE: 6

Ile Asp Gln Leu Glu Cys Thr Thr
                5

<210> SEQ ID NO 7
<211> LENGTH: 24
<212> TYPE: DNA
<213> ORGANISM: Artificial Sequence
<220> FEATURE:
<223> OTHER INFORMATION: nucleotide sequence for anti-viral sense L gene
      segment MP-12Lvc of RVFV strain MP-12

<400> SEQUENCE: 7
gagctattct tagagtataa gaag                                          24

<210> SEQ ID NO 8
<211> LENGTH: 24
<212> TYPE: DNA
<213> ORGANISM: Artificial Sequence
<220> FEATURE:
<223> OTHER INFORMATION: nucleotide sequence for anti-viral L gene
      segment MP-12Lvc of recombinant RVFV strain rMP-12

<400> SEQUENCE: 8
gagctattcc tcgagtataa gaag                                          24

<210> SEQ ID NO 9
<211> LENGTH: 8
<212> TYPE: PRT
<213> ORGANISM: Artificial Sequence
<220> FEATURE:
<221> NAME/KEY: CHAIN
<223> OTHER INFORMATION: amino acid sequence within an L protein of
      RVFV strain MP-12

<400> SEQUENCE: 9

Glu Leu Phe Leu Glu Tyr Lys Lys
                5

<210> SEQ ID NO 10
<211> LENGTH: 15
<212> TYPE: RNA
<213> ORGANISM: Artificial Sequence
<220> FEATURE:
<222> LOCATION: 65..79
<223> OTHER INFORMATION: nucleotide sequence within RVFV clone MP12-C13

<400> SEQUENCE: 10
uugcagagug gucgu                                                    15

<210> SEQ ID NO 11
<211> LENGTH: 12
<212> TYPE: RNA
<213> ORGANISM: Artificial Sequence
<220> FEATURE:
<222> LOCATION: 629..640
<223> OTHER INFORMATION: nucleotide sequence within RVFV clone MP12-C13

<400> SEQUENCE: 11
cacgcagcaa aa                                                       12

<210> SEQ ID NO 12
<211> LENGTH: 5
<212> TYPE: PRT
<213> ORGANISM: Artificial Sequence
<220> FEATURE:

-continued

```
<221> NAME/KEY: CHAIN
<223> OTHER INFORMATION: N-terminal sequence within RVFV clone MP12-C13

<400> SEQUENCE: 12

Leu Gln Ser Gly Arg
              5

<210> SEQ ID NO 13
<211> LENGTH: 4
<212> TYPE: PRT
<213> ORGANISM: Artificial Sequence
<220> FEATURE:
<221> NAME/KEY: CHAIN
<223> OTHER INFORMATION: C-terminal sequence within RVFV clone MP12-C13

<400> SEQUENCE: 13

Gln Ala Ala Lys

<210> SEQ ID NO 14
<211> LENGTH: 33
<212> TYPE: RNA
<213> ORGANISM: Artificial Sequence
<220> FEATURE:
<223> OTHER INFORMATION: nucleotide sequence within recombinant
      RVFV clone rMP12-C13type

<400> SEQUENCE: 14
uugcagagug gucgugcagu ccaagcagca aaa                                   33

<210> SEQ ID NO 15
<211> LENGTH: 11
<212> TYPE: PRT
<213> ORGANISM: Artificial Sequence
<220> FEATURE:
<221> NAME/KEY: CHAIN
<223> OTHER INFORMATION: amino acid sequence within recombinant
      RVFV clone rMP12-C13type

<400> SEQUENCE: 15

Leu Gln Ser Gly Arg Asp Val Gln Ala Ala Lys
              5                  10

<210> SEQ ID NO 16
<211> LENGTH: 16
<212> TYPE: RNA
<213> ORGANISM: Artificial Sequence
<220> FEATURE:
<222> LOCATION: 21..36
<223> OTHER INFORMATION: nucleotide sequence within RVFV MP-12

<400> SEQUENCE: 16
uaucaaguau aucaug                                                      16

<210> SEQ ID NO 17
<211> LENGTH: 13
<212> TYPE: RNA
<213> ORGANISM: Artificial Sequence
<220> FEATURE:
<222> LOCATION: 820..832
<223> OTHER INFORMATION: nucleotide sequence within RVFV MP-12

<400> SEQUENCE: 17
ugagguugau uag                                                         13

<210> SEQ ID NO 18
<211> LENGTH: 28
<212> TYPE: RNA
<213> ORGANISM: Artificial Sequence
```

```
<220> FEATURE:
<223> OTHER INFORMATION: nucleotide sequence within RVFV NSs deletion
      mutant rMP-12-NSdel

<400> SEQUENCE: 18
uaucaagguu cuaguugagg uugauuag                                             28

<210> SEQ ID NO 19
<211> LENGTH: 7
<212> TYPE: RNA
<213> ORGANISM: Artificial Sequence
<220> FEATURE:
<223> OTHER INFORMATION: nucleotide sequence within RVFV anti-genomic-
      sense arMP-12 and anti-genomic-sense NS deletion
      mutants arMP-12-delNSm-1 and arMP-12-delNSm-2

<400> SEQUENCE: 19 uaaaugu                                                                     7

<210> SEQ ID NO 20
<211> LENGTH: 7
<212> TYPE: RNA
<213> ORGANISM: Artificial Sequence
<220> FEATURE:
<223> OTHER INFORMATION: nucleotide sequence within RVFV anti-genomic-
      sense arMP-12 and anti-genomic-sense 78KD protein
      deletion mutant arMP-12-del78

<400> SEQUENCE: 20 gagauga                                                                     7

<210> SEQ ID NO 21
<211> LENGTH: 7
<212> TYPE: RNA
<213> ORGANISM: Artificial Sequence
<220> FEATURE:
<223> OTHER INFORMATION: nucleotide sequence within anti-genomic-sense
      NSs deletion mutant arMP-12-delNSm-1

<400> SEQUENCE: 21 gagguga                                                                     7

<210> SEQ ID NO 22
<211> LENGTH: 7
<212> TYPE: RNA
<213> ORGANISM: Artificial Sequence
<220> FEATURE:
<223> OTHER INFORMATION: nucleotide sequence within anti-genomic-sense
      NSs deletion mutant arMP-12-delNSm-2 and anti-genomic-
      sense NSs/78kD deletion mutant arMP-12-delNSm/78

<400> SEQUENCE: 22 gaggcca                                                                     7

<210> SEQ ID NO 23
<211> LENGTH: 7
<212> TYPE: RNA
<213> ORGANISM: Artificial Sequence
<220> FEATURE:
<223> OTHER INFORMATION: nucleotide sequence within anti-genomic-sense
      78kD protein deletion mutant arMP-12-delNSm-2 and anti-
      genomic-sense NSs/78kD deletion mutant
      arMP-12-delNSm/78

<400> SEQUENCE: 23 ugaauuc                                                                     7

<210> SEQ ID NO 24
```

```
<211> LENGTH: 18
<212> TYPE: DNA
<213> ORGANISM: Artificial Sequence
<220> FEATURE:
<221> NAME/KEY: primer_binding
<223> OTHER INFORMATION: nucleotide sequence of M18F primer

<400> SEQUENCE: 24
acacaaagac ggtgcatt                                                 18

<210> SEQ ID NO 25
<211> LENGTH: 22
<212> TYPE: DNA
<213> ORGANISM: Artificial Sequence
<220> FEATURE:
<221> NAME/KEY: primer_binding
<223> OTHER INFORMATION: nucleotide sequence of M159R primer

<400> SEQUENCE: 25
gtgaatccca agctccttca at                                            22
```

REVERSE GENETIC SYSTEM FOR RIFT VALLEY FEVER VIRUS AND USES THEREOF

CROSS REFERENCE TO RELATED APPLICATION

This non-provisional application claims benefit of provisional application U.S. Ser. No. 60/740,853 filed on Nov. 30, 2005, now abandoned.

FEDERAL FUNDING LEGEND

This invention was produced using funds obtained through a National Institutes of Health Grant (U54 AI057156). Consequently, the Federal government has certain rights in this invention.

BACKGROUND OF THE INVENTION

1. Field of the Invention

The present invention relates generally to the field of molecular biology, virology and immunology. More specifically, the present invention provides a reverse genetic system for Rift Valley fever virus (RVFV) and discloses its use in the development of vaccine for Rift Valley fever virus and in the large scale screening of antivirals and developing a marker for Rift Valley fever virus.

2. Description of the Related Art

Rift Valley fever virus causes an endemic disease of sub-Saharan Africa that has emerged in explosive mosquito-borne epidemics resulting not only in massive economic loss in herds of sheep and cattle but also causing hemorrhagic fever, encephalitis, retinal vasculitis and lesser disease in humans. In addition to the epidemics in sub-Saharan Africa, Rift Valley fever virus has been exported to Egypt on multiple occasions, particularly in 1977 when thousands of human infections occurred (Peters and Meegan, 1981). After a large epidemic in Africa in 1997-1998, the virus traveled to Egypt and the Arabian peninsula, menacing further spread (Shoemaker et al., 2002; Woods et al., 2002). The possibilities of introduction in many different countries and of its use as a bioterrorist agent (Peters, 2000) demand the availability of effective protective measures for humans and domestic animals.

It is likely that the disease can only be controlled by an effective live attenuated vaccine for livestock and certainly the control activities will necessitate protection of humans, most likely by vaccination (Peters, 1997). The livestock vaccines that are available are unsatisfactory either because of fetal pathology or lack of immunogenicity and because modern usage of vaccines requires the presence of markers to identify vaccinated animals in contrast to those after natural infection. Furthermore, the development of vaccine is also hampered due to lack of knowledge of the basis of attenuation of the single viable human vaccine candidate (Caplen et al., 1985; Vialat et al., 1997). Another major barrier to the development of vaccine for Rift Valley fever virus is the lack of understanding of the molecular virology of Bunyaviridae and of its medically important genus *Phlebovirus*.

Reverse genetics has been established for several RNA virus families, but Arenaviridae and Bunyaviridae have been recalcitrant. Among the family Bunyaviridae, only Bunyamvera virus (BUN) (Bridgen and Elliott, 2001) and La Crosse virus (LAC) (Blakqori and Weber, 2005) belonging to the genus *Orthobunyavirus* have been successfully recovered from cDNA. So far no viruses from the other four Bunyaviridae genera have been recovered. The *Phlebovirus* genus, in particular, that has a number of important human and animal pathogens, is poorly understood at the molecular level and unlike other Bunyaviridae has a replication strategy that resembles arenaviruses and utilizes an ambisense coding strategy (Schmaljohn and Hooper, 2001).

Thus, prior art is deficient in a Rift Valley fever virus expression system that can be used to develop vaccines for Rift Valley fever virus, screen antivirals and develop markers for Rift Valley fever virus. The current invention fulfils this long standing need in the art.

SUMMARY OF TH INVENTION

In one embodiment of the present invention, there is provided a reverse genetic system for a *Phlebovirus*. Such a system comprises anti-viral sense RNA expression plasmids either alone or in combination with viral structural protein expression plasmids. In a related embodiment of the present invention, there is provided a host cell comprising and expressing the plasmids of the reverse genetic system described supra.

In yet another related embodiment of the present invention, there is a method of evaluating function of a Phleboviral gene in an organism. Such a method comprises generating viruses that express the gene or lack the expression of the gene of interest using the reverse genetic system described supra. The organism is then infected with the altered virus and the effect of over-expressing or knocking out the gene in the organism is then determined, thereby evaluating the function of the gene in the organism.

In still yet another related embodiment of the present invention, there is a method of generating a Phleboviral vaccine. Such a method comprises generating an immunogenic composition comprising an attenuated *Phlebovirus* using the reverse genetic system described supra; and administering immunologically effective amounts of the immunogenic composition to a subject, where the composition induces a protective immune response against the *Phlebovirus* in the subject, thereby generating the Phleboviral vaccine. In yet another related embodiment of the present invention, there is an immunogenic composition comprising the Phleboviral vaccine generated by the method described supra.

In another embodiment of the present invention, there is a reverse genetic system for a *Phlebovirus*. Such a system comprises anti-viral sense RNA expression plasmids either alone or in combination with viral structural protein expression plasmids, where the RNA expression plasmid encodes a non-viral foreign gene.

In another related embodiment of the present invention, there is provided a host cell comprising and expressing the plasmids of the reverse genetic system described supra. In still another related embodiment of the present invention, there is provided an infectious clone encoding a recombinant *Phlebovirus* generated using the reverse genetic system described supra. In yet another related embodiment of the present invention, there is provided a method of generating a *Phlebovirus*-based expression vector. This method comprises generating a recombinant *Phlebovirus* expressing a nonviral foreign protein using the reverse genetic system described supra, where the non-viral foreign gene is inserted in place of the S segment NSs ORF in the anti-viral sense RNA expression plasmid.

In another related embodiment of the present invention, there is provided an expression vector, comprising: a nucleotide sequence that encodes a recombinant *Phlebovirus* generated using the reverse genetic system described supra. In yet another related embodiment of the present invention, there is provided a method of determining presence of antibody to *Phlebovirus* in a subject. This method comprises obtaining serum sample from the subject; and performing assay using the expression vector described supra to determine presence or absence of antigenic reactions, effect on physical properties of the *Phlebovirus* or a combination thereof in the serum sample, thereby determining the presence of antibody to *Phlebovirus* in the subject.

In still yet another related embodiment of the present invention, there is provided a method of screening compounds that can be used as anti-*Phlebovirus* drugs. This method comprises incubating the compounds with the expression vector described supra; and determining the effect of the compound on the replication, the physical properties or combinations thereof of the *Phlebovirus*, thereby screening compounds that can be used as anti-*Phlebovirus* drugs.

In another related embodiment of the present invention, there is a kit comprising the expression vector described supra. In yet another related embodiment of the present invention, there is an immunogenic composition comprising the expression vector described supra. In yet another related embodiment of the present invention, there is provided a method of generating Phleboviral marker vaccine. Such a method comprises administering immunologically effective amounts of the immunogenic composition described supra to a subject, where the composition induces a protective immune response against the *Phlebovirus* in the subject and identifies the vaccinated subject, thereby generating a Phleboviral marker vaccine.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 1A-1C show introduction of gene marker into S, M and L segments. FIG. 1A shows alignment of sequences of nucleotide and amino acid (aa). Xho I sites that were introduced on viral-sense S (Sv; SEQ ID NO: 1 and 2 (nucleotide); SEQ ID NO: 3 (aa)), anti-viral-sense M (Mvc; SEQ ID NO: 4 and 5 (nucleotide); SEQ ID No: 6 (aa)) and anti-viral sense L (Lvc; SEQ ID NO: 7 and 8 (nucleotide); SEQ ID NO: 9 (aa)) segments are underlined. Positions of mutations are shown as arrowheads. FIG. 1B shows Xho I marker in rMP-12 RNA. Viral RNA was extracted from culture supernatants of Vero E6 cells infected with MP-12 and rMP-12. After digesting RNA with DNase I at 37° C. for 1 hr, PCR was performed with and without reverse transcription step (RT). Water was used as a negative control. Digestion with XhoI was performed at 37° C. for 2 hr. Expected sizes of XhoI-digested fragments are shown to the right of the gels. FIG. 1C demonstrates XhoI marker in rMP-12 without using protein expression plasmids listed in Table 1, plasmid combination D.

FIGS. 2A-2D show production of NSs deletion mutants. FIG. 2A shows diagram of NSs deletion mutants. FIG. 2B shows alignment of nucleotide (nt) and amino acid (aa) sequences between Clone 13 (C13; SEQ ID NO: 10 and 11 (nt); SEQ ID NO: 12 and 13 (aa)) and rMP12-C13 type (SEQ ID NO: 14 (nt); SEQ ID NO: 15 (aa)) or MP-12 (SEQ ID NO: 16 and 17 (nt)) and rMP-12NSdel (SEQ ID NO: 18 (aa)). Additional sequences in the mutants are underlined. The rMP-12-NSdel does not contain first AUG (methionine:M) and does not produce NSs protein. N-term, N-terminal; C-term, C-terminal. FIG. 2C shows purified virion RNA of MP-12, rMP-12, rMP-12-C13 type and rMP-12-NSdel that were analyzed by Northern blotting using viral-sense S, M and L-specific RNA probes (Ikegami et al., 2005). FIG. 2D shows results of Western blot analysis using anti-NSs, anti-RVFV and anti-actin antibodies (Ikegami et al., 2005). Vero E6 cells were infected with MP-12 and the mutants at an MOI of 1 and were harvested at 6 hpi.

FIGS. 3A-3B show production of recombinant MP-12 expressing *Renilla* luciferase. FIG. 3A is a diagrammatic representation of the S-segment of rMP-12-rLuc. *Renilla* luciferase open reading frame with HpaI and SpeI sites at 5' and 3' ends, respectively was inserted into the cassette of S-segmant digested with HpaI and SpeI. FIG. 3B shows luciferase activities tested at several time points when Vero cells were infected with rMP-12-rLuc or MP-12 at the MOI indicated in the parenthesis. Luciferase activities of $3.2 \times 10^4$ cells and $1.6 \times 10^3$ cells are shown for early (upper panel) and late (lower panel) time points, respectively.

FIGS. 4A-4D shows growth curve of MP-12 and the mutants. Vero cells (FIG. 4A), 293 cells (FIG. 4B) and MRC-5 cells (FIGS. 4C and 4D) were infected with MP-12, rMP-12, rMP-12-C13 type, rMP-12-NSdel and rMP-12-rLuc at an MOI of 1 (FIGS. 4A, 4B and 4C) or 0.01 (FIG. 4D) and the culture supernatants were collected at the time points shown. Culture supernatants were collected from three independent wells at each time point and the viral plaque titer determined by assay in Vero E6 cells. The graph shows the mean titers +/– standard deviation from three independent experiments.

FIG. 5 shows accumulation of IFN-β mRNA and TNF-α mRNa in MRC-5 cells infected with NSs deletion mutants. MRC-5 cells were mock infected (Mock) or infected with rMP-12, rMP12-C13 type and rMP12-NSdel at an MOI of 1. Total ontracellular RNAs were extracted at indicated times (hours p.i.). RNA samples were hybridized with multipore template (hCK-3) and Rnase protection assay was performed. P, probes; TGFβ3, transforming growth factor β3; GAPDH, glyceraldehyde-3-phosphate dehydrogenase.

FIGS. 6A-6B show responses of host cells infected with MP-12 and the mutants. FIG. 6A shows plaque production in Vero E6 cells by MP-12, rMP-12, rMP-12-C$_{13}$ type and rMP12-NSdel stained with neutral red and crystal violet. FIG. 6B shows shutoff of host protein synthesis. Vero cells were mock infected (Mock) or infected with MP-12, rMP-12, rMP12-C13type and rMP-12-NSdel at an MOI of 5. Cells were labeled with 100 µCi/ml of [$^{35}$S] methionine for 1 h at 17 h post infection. Cell extracts were analyzed on 10% polyacrylamide gel. The positions of synthesized of N and NSs proteins are shown by arrowheads to the right of the gel.

FIG. 7 shows schematic representation of the MP-12 antigenomic-sense M segment and sequences of the pre-Gn region sections. Five in-frame translation initiation codons in the pre-Gn region are illustrated by five short vertical lines. Regions that encode the NSm and 78-kDa proteins are represented by two boxes at the top. The sequences around the first and second AUGs in the pre-Gn region are shown at the bottom. The nucleic acid sequence of arMP-12 is shown in SEQ ID NO: 19 and SEQ ID NO: 20. Nucleotide substitutions in arMP-12-delNSm-1 (SEQ ID NO: 19 and SEQ ID NO: 21) and arMP-12-delNSm-2 (SEQ ID NO: 19 and SEQ ID NO: 22) at the second AUG were, respectively, GUG and GCC. An EcoRI sequence was introduced into the first AUG in arMP-12-del78 (SEQ ID NO: 23 and SEQ ID NO: 20). arMP-12-delNSm/78 (SEQ ID NO: 23 and SEQ ID No: 22) had mutations at both the first and second AUGs as indicated.

FIGS. 8A-8D show plaque phenotype and protein expression of mutant viruses. In FIG. 8A, Vero E6 cells were infected with arMP-12 and its mutant viruses as indicated. Plaques were stained with crystal violet at 3 days p.i. In FIG. 8B, Vero E6 cells were mock-infected (Mock) or independently infected with the indicated viruses at an m.o.i. of 1, and cell extracts were prepared using lysis buffer (1% Triton X-100, 0.5% sodium deoxycholate, 0.1% SDS in phosphate-buffered saline) at 24 h p.i. Viral proteins were separated on 12% SDS-polyacrylamide gel electrophoresis (SDS-PAGE). Western blot analysis was performed using anti-NSm antibody to demonstrate NSm and 78-kDa protein. The asterisk represents a protein of unknown origin, which was recognized by anti-NSm antibody. In FIG. 8C, Vero E6 cells were mock-infected (Mock) or infected with the indicated viruses at an m.o.i. of 1, and the cells were labeled with 100 μCi/ml of Tran$^{35}$S-label for 30 min at 8 h p.i. MP-12-specific N, Gn and Gc proteins were immunoprecipitated using anti-N polyclonal antibody (anti-N), anti-Gn monoclonal antibody (anti-Gn) and anti-Gc monoclonal antibody (anti-Gc), respectively. Anti-Gn antibody also efficiently precipitated the 78-kDa protein (dots). Anti-RVFV antibody (anti-RVFV) (Ikegami et al., 2005) was used to immunoprecipitate Gn, Gc and N proteins of arMP-12 and its mutant viruses. Normal mouse serum (Normal serum) was used as a control. Precipitated proteins were analyzed on 10% SDS-PAGE. In FIG. 8D, Vero E6 cells were mock-infected (Mock) or independently infected with indicated viruses at an m.o.i. of 1, and cell extracts were prepared at 8 h p.i. Western blot analysis was performed using anti-Gn monoclonal antibody, anti-Gc monoclonal antibody and anti-actin antibody to detect Gn protein, Gc protein and actin, respectively.

FIG. 10A shows the structure of the 5'-end of the antigenomic sense M segment of arMP-12 and that of arMP-12-delNSm/78 and binding sites of two primers, M18F (5'-ACACAAA-GACGGTGCATT-3'; SEQ ID NO: 24) and M159R (5'-GT-GAATCCCAAGCTCCTTCAAT-3'; SEQ ID NO: 25) at the top. EcoR I digestion of the arMP-12-delNSm/78-derived PCR product, but not of the arMP-12-derived PCR product, generated 140-bp long and 19-bp long PCR fragments (bottom). FIG. 10B shows results of a competition-propagation assay that was performed as described herein. Vero E6 cells were mock-infected (Mock), independently infected with arMP-12 (arMP-12) or arMP-12-delNSm/78 (delNSm/78), coinfected with arMP-12 and arMP-12-delNSm/78 at the indicated ratio ($P_0$), with virus samples passaged three times ($P_3$) or with those passaged five times ($P_5$). For extraction of intracellular RNAs, viruses were infected at an m.o.i. of 1, while virus passage was performed at an m.o.i. of 0.1. Intracellular RNA was extracted at 8 h p.i. by using Trizol Reagent (Invitrogen). After DNase I digestion of the samples, cDNA was synthesized using random hexamers and superscript II reverse transcriptase (Invitrogen) at 42° C. for 1 hr. The 5'-end of the antigenomic sense M segment was amplified from these cDNAs and plasmids pPro-T7-avM(+) [pT7-avM(+)] and pPro-T7-avM(+)-EcoRI [pT7-avM(+)-EcoRI] with primer set, M18F/M159R, and Expand High Fidelity PCR system (Roche Applied Science); PCR was performed 95° C. for 3 min, followed by 30 cycles of 95° C. for 40 s, 55° C. for 1 min and 72° C. for 30 s. The PCR products were digested with EcoRI, and the samples were analyzed by 2% agarose gel electrophoresis.

FIG. 11 shows radioimmunoprecipitation analysis of cells infected with MP-12 and its deletion mutant viruses.

FIG. 12 shows analysis of cytokine production from rMP-12-infected J774.1 cells and from rMP-12-del21/382-infected J774.1 cells.

FIG. 13 shows northern blot analysis of intracellular MP-12-specific RNAs and intracellular ZH501-specific RNAs. Lvc, antiviral-sense L RNA; Mvc, antiviral-sense M RNA; Svc, antiviral-sense S RNA; Lv, viral-sense L RNA; Mv, viral-sense M RNA; Sv, viral-sense S RNA; N, N mRNA.

FIGS. 14A-14E shows western blot analysis of virus-specific proteins in MP-12-infected cells and ZH501-infected cells. FIG. 14A: anti-RVFV antibody; FIG. 14B: anti-NSs antibody; FIG. 14C: anti-RVFV antibody; FIG. 14D: anti-Gn monoclonal antibody; FIG. 14E: anti-alpha actin antibody

DETAILED DESCRIPTION OF THE INVENTION

Figure 1B:
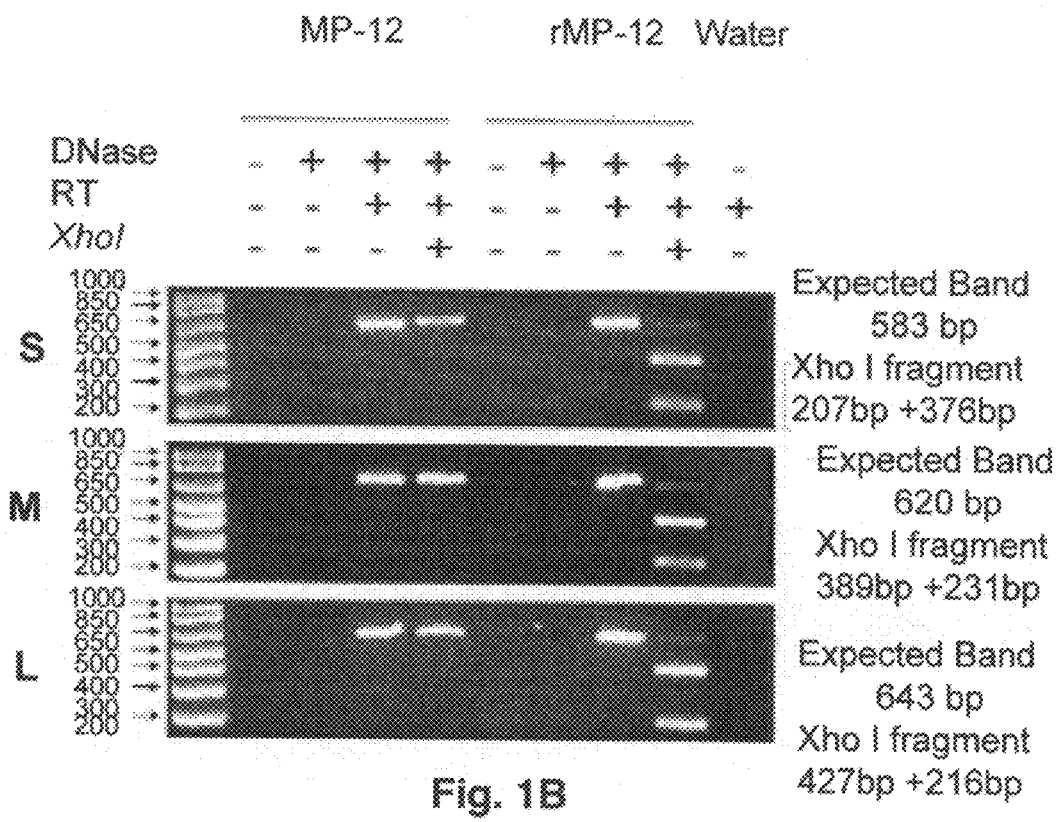

Control of Rift Valley fever virus after either a natural introduction or a bioterrorist attack would require protection of humans as well as livestock (Peters, 1997). Although there is an activated Rift Valley fever virus vaccine that has been widely used in laboratory workers, that immunogen is no longer available (Pittman et al., 1999). An attenuated vaccine, MP-12 is safe and immunogenic but requires further development (Caplen et al., 1985; Morrill and Peters, 2003). One of the critical elements of understanding the safety profile of this candidate as a human vaccine is to understand the significance of its more than 40 point mutations for attenuation (Vialat et al., 1997). This task and the additional development of a veterinary vaccine are dependent on a reverse genetics system.

The present invention describes a Rift Valley fever virus reverse genetics system, the first for the viruses of the *Phlebovirus* genus. Infectious Rift Valley fever virus was consistently rescued by cotransfecting plasmids encoding anti-viral sense RNA segments and plasmids expressing L, N, and envelope proteins into BHK/T7-9 cells that stably express T7 RNA polymerase (Ito et al., 2003), while rescue of the infectious virus did not occur after co-transfection of 293T or BHK-21 cells with pCT7pol plasmid encoding T7 RNA polymerase along with other protein-expressing and RNA-expressing plasmids. However, it was unclear why the virus rescue failed using transient T7 polymerase expression.

When the cells were co-transfected with plasmids bearing Rift Valley fever virus structural protein genes and a plasmid expressing viral minigenome encoding green fluorescent protein (GFP) ORF, production of virus-like particles carrying a viral minigenome was more efficient in BHK/T7-9 cells than 293T or BHK-21 cells transiently expressing T7 polymerase, implying that virus assembly in BHK/T7-9 cells was more active than the latter two cells. Not all BHK-derived cell lines constitutively expressing T7 polymerase were suitable for virus rescue, because no infectious viruses were obtained using BHK-21 cells expressing high levels of T7 polymerase induced by an Eastern equine encephalitis virus replicon.

Although the first reverse genetics system of BUN used vaccinia virus expressing T7 polymerase (Bridgen and Elliott, 1996), all recent bunyavirus reverse genetic systems including the present invention used BHK cells that stably express T7 polymerase without using any virus vectors (Blakqori and Weber, 2005; Lowen et al., 2004). The mechanisms for this success are unknown but the practical implications are obvious. Transfection of protein-expression plasmids inhibited LAC rescue (Blakqori and Weber, 2005) but had no effect on rescue of infectious BUN (Lowen et al., 2004). Cotransfection of protein expression plasmids and RNA expression plasmids resulted in consistent recovery of MP-12 (Tables 1 and 2). Infectious viruses were also recovered in the absence of protein expression plasmids, although virus rescue was not always successful (Table 1). In both BUN (Bridgen and Elliott, 1996; Lowen et al., 2004) and LAC (Blakqori and Weber, 2005) reverse genetics systems, infectious viruses are produced only from cells that express anti-viral sense RNA transcripts, whereas infectious MP-12 was recovered from cells expressing viral-sense RNA transcripts and anti-viral-sense RNA transcripts (Table 1). These studies indicated that requirements and optimal conditions for virus recovery very among Bunyaviridae.

Since NSs protein expression promotes Rift Valley fever virus minigenome RNA synthesis in various cell lines, it was predicted that NSs protein expression would be important for a successful Rift Valley fever virus reverse genetics system (Ikegami et al., 2005). In contrast to this prediction, NSs protein expression suppressed virus recovery (Table 1). Interestingly, since NSs protein expression did not increase or decrease minigenome RNA replication in BHK/T7-9 cells, it was unclear why NSs protein expression inhibited the rescue of infectious viruses.

The Rift Valley fever virus mutant clone 13 carrying an in-frame deletion of about 70% of the NSs gene is viable and fails to inhibit host mRNA transcription (Bilecocq et al., 2004; Le May et al., 2004) and has markedly reduced virulence in interferon competent mice (Bouloy et al., 2001). Nevertheless, it was unclear whether some portion of the NSs protein and/or its coding region is necessary for virus replication. The present invention demonstrated that rMP12-Nsdel and rMP12-rLuc, both of which lacked the NSs gene ORF, replicated efficiently in Vero and 293 cells (FIGS. 4A and 4B); the former replicated slightly less well than MP-12, yet the later grew to similar levels as MP-12. These data demonstrated that NSs protein and its coding region were dispensable for Rift Valley fever virus replication.

In contrast to Vero and 293 cells, both rMP12-C13type and rMP12-NSdel did not replicate efficiently in MRC-5 cells (FIGS. 4C and 4D) and failed to inhibit the accumulation of IFNβ and TNFα mRNAs (FIG. 5), strongly suggesting that IFNβ was released from infected MRC-5 cells and suppressed replication of these mutant viruses. These data were consistent with a previous report that clone 13 does not grow well in MRC-5 cells (Muller et al., 1995), Efficient replication of those mutant viruses lacking NSs gene in Vero cells was most probably due to the absence of IFNαβ gene in this cell line (Diaz et al., 1988; Mosca and Pitha, 1986). Because 293 cells were able to accumulate IFNβ mRNA after Sendai virus infection (data not shown), IFNβ was probably released from 293 cells that were infected with MP-12 mutants lacking NSs gene. Nevertheless, replication of those mutants was not suppressed in 293 cells. It is possible that the induction of IFNβ-induced antiviral responses in 293 cells may not be as efficient as MRC-5 cells, but further studies will be needed to test this possibility.

MP-12 is a highly attenuated virus and mutations in all three viral RNA segments contribute to its attenuation (Peters, 1997; Saluzzo and Smith, 1990). It has been demonstrated that wt RVFV NSs can decrease general host transcription (Le May et al., 2004), suppresses IFNβ promoter activation without inhibiting activities of interferon regulatory factor 3, NF-kB and ATF2/cJun (AP-1) (Bilecocq et al., 2004) and is a major virus virulence factor (Blakqori and Weber, 2005). There is one amino acid difference between wt RVFV ZH548 NSs protein and MP-12 NSs protein (Vialat et al., 1997), hence possibilities exist that this amino acid substitution alters biological functions of NSs and contributes to the attenuation of MP-12. Like wt RVFV, MP-12 NSs protein was responsible for inhibition of IFNb mRNA accumulation (FIG. 5) and host protein synthesis shut-off (FIG. 6B) demonstrating that the amino acid substitution in MP-12 NSs did not alter all biological functions of NSs. The effect of this amino acid substitution in virus virulence remains to be investigated.

Furthermore, it was also unclear why the plaques of rMP12-C13type and rMP12-NSdel were larger than those of MP-12 and rMp-12 (FIG. 6A, upper panels). MP-12 strain was selected for larger plaques (Caplen et al., 1985) and they are larger than wild type Rift Valley fever virus strain (Rossi and Turell, 1988). However, Rift Valley fever virus isolates from nature or laboratory variants forming smaller plaques are usually attenuated in animals (Rossi and Turell, 1988). Apparently, plaque size has no obligatory correlation with virulence of Rift Valley fever virus. Although LAC and BUN, both of which belong to the genus *Orthobunyavirus* do not use an ambisense strategy for NSs protein expression and the sizes and amino acid sequences of their NSs proteins differ from those of Rift Valley fever virus (genus *Phlebovirus*), LAC (Blakqori and Weber, 2005) and BUN (Bridgen et al., 2001) lacking NSs are also viable.

Taking advantage of the ambisense strategy of the s RNA segment gene expression and the NSs gene ORF being dispensable for virus replication, a rMP12-rLuc, which expressed enzymatically active luciferase in infected cells was generated. This was the first demonstration of foreign gene expression in any bunyavirus. Consistent with the report that NSs mRNA synthesis occurs early in infection using the virion-associated anti-viral-sense S segment as a template (Ikegami et al., 2005), luciferase activity was detectable as early as 60 min pi of rMP12-rLuc (FIG. 3B). rMP12-rLuc replicated as efficiently as MP-12 in Vero cells and 293 cells, it stably retained the inserted rLuc ORF after 10 virus passages and it can be handled in a biosafety level 2 lab.

In brief, an objective of the present invention was to manipulate any desired sequence of Rift Valley fever virus to generate new Rift Valley fever viruses. In order to accomplish this, the present invention developed a reverse genetic system of a vaccine strain of Rift Valley fever virus, MP12. In this system, BHK cells that constitutively express T7 polymerase were cotransfected with three RNA expression plasmids, each encoding MP12 L, M, or S segments, in antiviral sense and three expression plasmids each expressing L, N or envelope proteins. Infectious viruses were released after 3-5 days of incubation and the titer of the virus was about $5 \times 10^4$ PFU/ml. The released viruses were not merely contamination by authentic MP12 from the laboratory, because a unique restriction site which was introduced into each of L, M and S segments of the RNA expression plasmids, was detected in the each three fragment of the recovered virus. Furthermore, the present invention also demonstrated that transfection of three RNA expression plasmids was sufficient for the recovery of the virus. Additionally, two mutant viruses were recovered in the present invention. One of the viruses had a complete deletion of NSs gene and the other had a deletion of about 70% of NSs; the deletion of the later mutant was the same as another Rift Valley fever virus mutant CL13. Both the deletion mutants replicated in Vero cells, yet their cytopathic effects were less severe as compared to MP12.

The present invention also characterized RVFVs carrying mutations of the M gene preglycoprotein region, one lacking NSm protein expression, one lacking 78-kDa protein and one lacking expression of both proteins. All of the mutants and their parent virus produced plaques with similar sizes and morphologies in Vero E6 cells and had similar growth kinetics in Vero, C6/36 and MRC5 cells, demonstrating that the NSm and 78-kDa proteins were not needed for the virus to replicate efficiently in cell culture. A competition-propagation assay revealed that the parental virus was slightly more fit than the mutant virus than the mutant virus lacking expression of both proteins.

It is contemplated that the present invention can be used to manipulate Rift Valley fever virus genomes, allow detailed studies of functions of all viral genes, allow study of Rift Valley fever virus pathogenicity and allow generating new Rift Valley fever virus vaccines. Additionally, although Rift Valley fever virus MP12 has been developed as a human Rift Valley fever virus vaccine, the system disclosed by the present invention will enable the development of a better human vaccine.

Furthermore, the present invention also demonstrated the use of the reverse genetic system to generate infectious MP12-expressing Luc protein (MP12-Luc). In order to do so, BHK cells that constitutively expressed T7 polymerase were cotransfected with three RNA expression plasmids each encoding L segment, M segment or S segment carrying Luc gene in the place of NSs ORF, in antiviral sense and three expression plasmids each expressing L, N or envelope proteins. MP12-Luc was recovered after 3-5 days of incubation. Infection of VeroE6 cells with MP12-Luc resulted in expression of Luc as early as 60 min post infection (p.i) and the Luc expression level substantially increased p.i. 120-240 min. These data clearly demonstrated that MP12-Luc expressed Luc protein in infected cells. This was the first demonstration of expression of a foreign gene by any member of the family Bunyaviridae. Moreover, the gene product was enzymatically active. Additionally, another recombinant MP-12 which has GFP ORF instead of NSs Orf was also produced. The inserted Gfp ORF was stable after 10 virus passages in Vero E6 cells and efficient GFP expression was detected throughout virus passages. It is contemplated that such MP-12 expressing foreign genes will be a valuable tool for rapid and large scale screening of antivirals against Rift Valley fever virus and rapid titration of neutralizing antibodies against Rift Valley fever virus in a biosafety level-2 lab and tracing of viral spread within susceptible host, such as interferon-deficient mice. These can also be used to study the molecular virology of RVFV, assess current vaccine candidates, produce new vaccines and incorporate marker genes into animal vaccines. Furthermore, it is also contemplated that the recombinant MP12 expressing a foreign gene will be used as an expression vector that allows expression of a foreign protein both in mammalian and insect cells and as marker vaccines to be used in veterinary arena allowing one to distinguish antibodies induced by an attenuated Rift Valley fever virus vaccine.

The present invention is directed to a reverse genetic system for a *Phlebovirus*, comprising: anti-viral sense RNA expression plasmids either alone or in combination with viral structural protein expression plasmids. Generally, the anti-viral sense RNA expression plasmids may individually encode a L segment, a M segment or a S segment of the *Phlebovirus*. Alternatively, the anti-viral sense RNA expression plasmids individually may comprise one or more than one single nucleotide polymorphism in the sequence encoding the L segment, the M segment or the S segment of the *Phlebovirus* or may comprise partial or complete deletions in the sequence encoding the L segment, the M segment or the S segment of the *Phlebovirus*. Furthermore, the viral structural protein expression plasmids may individually express a L protein, a N protein or envelope proteins of the *Phlebovirus*. Generally, the anti-viral sense RNA expression plasmid and the viral structural plasmid may be derived from pathogenic *Phleboviruses*. Additionally, examples of the pathogenic *Phleboviruses* are not limited to but may include River Valley fever virus, Punta Toro virus, Sandfly virus, and Toscana virus. Furthermore, the strain of the Rift Valley fever virus used in deriving such plasmids may be a wild type strain. Specifically, examples of the wild type strains of the River Valley fever virus are not limited to but may include MP-12 strain, ZH548, ZH501, SA75, or SPB 9800523.

The present invention is also directed to a host cell comprising and expressing the plasmids of the reverse genetic system described supra. Generally, the host cell may be a T7 polymerase expressing cell. Examples of such a host cell is not limited to but may include a BHK cell.

The present invention is further directed to a method of evaluating function of a Phleboviral gene in an organism, comprising: generating viruses that express the gene or lack the expression of the gene of interest using the reverse genetic system described supra, infecting the organism with the altered virus, and determining the effect of over-expressing or knocking out the gene in the organism, thereby evaluating the function of the gene in the organism. Generally, the gene whose function is evaluated may be a gene that affects pathogenicity of the virus, replication of the virus in different cultures or combinations thereof.

The present invention is still further directed to a method of generating Phleboviral vaccines, comprising: generating an immunogenic composition comprising an attenuated *Phlebovirus* using the reverse genetic system described supra; and administering immunologically effective amounts of the immunogenic composition to a subject, where the composition induces a protective immune response against the *Phlebovirus* in the subject, thereby generating the Phleboviral vaccine. Generally, the subject may be a human. Furthermore, the subject is likely to be exposed, suspected or diagnosed with an infection caused by the *Phlebovirus*. The reverse genetic system due to its ability to introduce specific mutations, assist in the safety profile determination of vaccine strains isolated naturally or by mutagenesis. Thus, one of skill in the art may introduce mutation(s) or single nucleotide polymorphisms and examine their individual contribution by either rescuing a wild virulent strain with a point mutation and examining attenuation and safety or remove a point mutation from an attenuated strain and observe its impact on reversion to virulence.

The present invention is further directed to an immunogenic composition comprising the Pheleboviral vaccine generated by the method described supra.

The present invention is also directed to a reverse genetic system for a *Phlebovirus*, comprising: anti-viral sense RNA expression plasmids either alone or in combination with viral structural protein expression plasmids, where the RNA expression plasmid encodes a non-viral foreign gene. Generally, the anti-viral sense RNA expression plasmids may individually encode a L segment, a M segment or the non-viral foreign gene that is inserted in place of a S segment NSs ORF. Further, the non-viral foreign gene may express a reporter protein. There are many reporter proteins that are being routinely used by in the art and can also be used by one of skill in the art in the construction of plasmids described herein. Hence, the examples of the reporter protein is not limited to but may include a *Renilla* luciferase or green fluorescent protein. Generally, the viral structural protein expression plasmids may individually express a L protein, a N protein or envelope protein of the *Phlebovirus*. Additionally, the plasmids described herein may be derived from pathogenic *Phlebovirus*. Examples of the viruses that the plasmids are derived from are the same as described supra. There are various pathogenic strains of the above-discussed viruses that are known in the art and discussed supra. Although the River Valley Fever virus is an MP-12 strain or a modified MP-12 strain, it is contemplated that one of skill in the art could use any of the pathogenic strains of the *Phleboviruses* to construct the plasmids described. Additionally, the host cell comprising and expressing these plasmids are the same as described supra. Furthermore, the present invention is also directed to an infectious clone encoding a recombinant *Phlebovirus* generated using the reverse genetic system described supra.

The present invention is further directed to a method of generating a *Phlebovirus*-based expression vector, comprising: generating a recombinant *Phlebovirus* expressing a non-viral foreign protein using the reverse genetic system described supra, where the non-viral foreign gene is inserted in place of the S segment NSs ORF in the anti-viral sense RNA expression plasmid. The present invention is still further directed to an expression vector, comprising: a nucleotide sequence that encodes a recombinant *Phlebovirus* generated using the reverse genetic system described supra. Such an expression vector may further comprise a nucleotide sequence encoding a protective antigen of a disease-causing agent. Further, examples of the disease-causing agent are not limited to but may include a naturally occurring *Phlebovirus*, Hepatitis B virus, or any disease causing viruses whose neutralizing antibody epitopes are identified. Examples of the recombinant *Phlebovirus* thus constructed is not limited to but includes MP12-Luc, MP-12 strain expressing luciferase, an MP-12 strain expressing Hepatitis B virus surface antigen or combinations thereof.

The present invention is also directed to a method of determining presence of antibody to *Phlebovirus* in a subject, comprising: obtaining serum sample from the subject; and performing assay using the expression vector described supra to determine presence or absence of antigenic reactions, effect on physical properties of the *Phlebovirus* or a combination thereof in the serum sample, thereby determining the presence of antibody to *Phlebovirus* in the subject. Examples of the assays that can be used in this method are not limited to but may include enzyme linked immunosorbent assay, neutralization test, or hemaglutination test. Generally, the subject may be a human.

The present invention is also directed to a method of screening compounds that can be used as anti-*Phlebovirus* drugs, comprising: incubating the compounds with the expression vector described supra; and determining the effect of the compound on the replication, physical properties or combinations thereof of the *Phlebovirus*, thereby screening the compounds that can be used as anti-*Phlebovirus* drugs.

The present invention is further directed to a kit, comprising: the expression vector described supra. The present invention is still further directed to an immunogenic composition comprising the expression vector of claim 31.

The present invention is also directed to a method of generating a Phleboviral marker vaccine, comprising: administering immunologically effective amounts of the immunogenic composition described supra to a subject, where the composition induces a protective immune response against the *Phlebovirus* in the subject and identifies the vaccinated subject, thereby generating a Phleboviral marker vaccine. Generally, the subject may be an animal, where the subject is likely to be exposed, suspected or diagnosed with an infection caused by the *Phlebovirus*.

As used herein, the term "a" or "an" may mean one or more. As used herein in the claim(s), when used in conjunction with the word "comprising", the words "a" or "an" may mean one or more than one. As used herein, the term "protective antigen" refers to an antigen that does not elicit an immune response.

The composition described herein may be administered independently one or more times to achieve, maintain or improve upon a therapeutic effect. It is well within the skill of an artisan to determine dosage or whether a suitable dosage of the composition and anti-cancer agent comprises a single administered dose or multiple administered doses. An appropriate dosage depends on the subject's health, the induction of immune response, the route of administration and the formulation used.

The following examples are given for the purpose of illustrating embodiments of the invention and do not limit the present invention in any fashion. One skilled in the art will appreciate readily that the present invention is well adapted to carry out the objects and obtain the ends mentioned, as well as those objects, ends and advantages inherent herein. Changes therein which are encompassed within the spirit of the invention as defined by the scope of the claims will occur to those skilled in the art.

EXAMPLE 1

Media, Cells and Viruses

Vero, Vero E6 293 (human embryonic kidney) and MRC-5 (human diploid fibroblast) cells were maintained in Dulbecco's modified minimum essential medium (DMEM) containing 10% fetal calf serum (FCS), BHK-21 cells and BHK/T7-9 cells which express T7 RNA polymerase (Ito et al., 2003) were grown in MEM-alpha containing 10% FCS. Penicillin (100 U/ml) and streptomycin (100 µg/ml) were added to the media. BHK-T7-9 cells were selected in medium containing 600 µg/ml hygromycin. RVFV vaccine strain MP-12 was grown in BHK-21 cells and infectivity was assayed by plaques in Vero E6 cells.

EXAMPLE 2

Plasmid

Figures 2A, 2B:
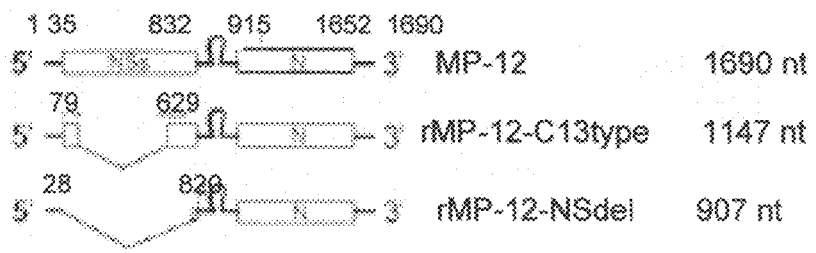

RVFV MP-12 strain full-length S, M and L segments were cloned between Kpn I and Not I sites of the pPro-T7 plasmid which originated from pSinRep5 (Invitrogen) to express full-length anti-viral-sense segments, resulting inpPro-T7-S(+), pPro-T7-M(+) and pPro-T7-L(+). A XhoI site was introduced into each of the S, M and L sequence by site-directed mutagenesis. The pPro-T7-S(−), pPro-T7-M(−) and pPro-T7-L(−) were constructed using a similar strategy. The pPro-T7-S(+)C13 was made by introducing two AatII sites into pPro-T7-S(+), digesting with AatII and self ligation (FIG. 2B). The pPro-T7-S(+)NSdel was made by introducing SpeI and HpaI near the ends of NSs ORF, digesting with SpeI and HpaI, filling in by T4 DNA polymerase and self-ligation (FIG. 2B).

Figures 2C, 2D, 3A:
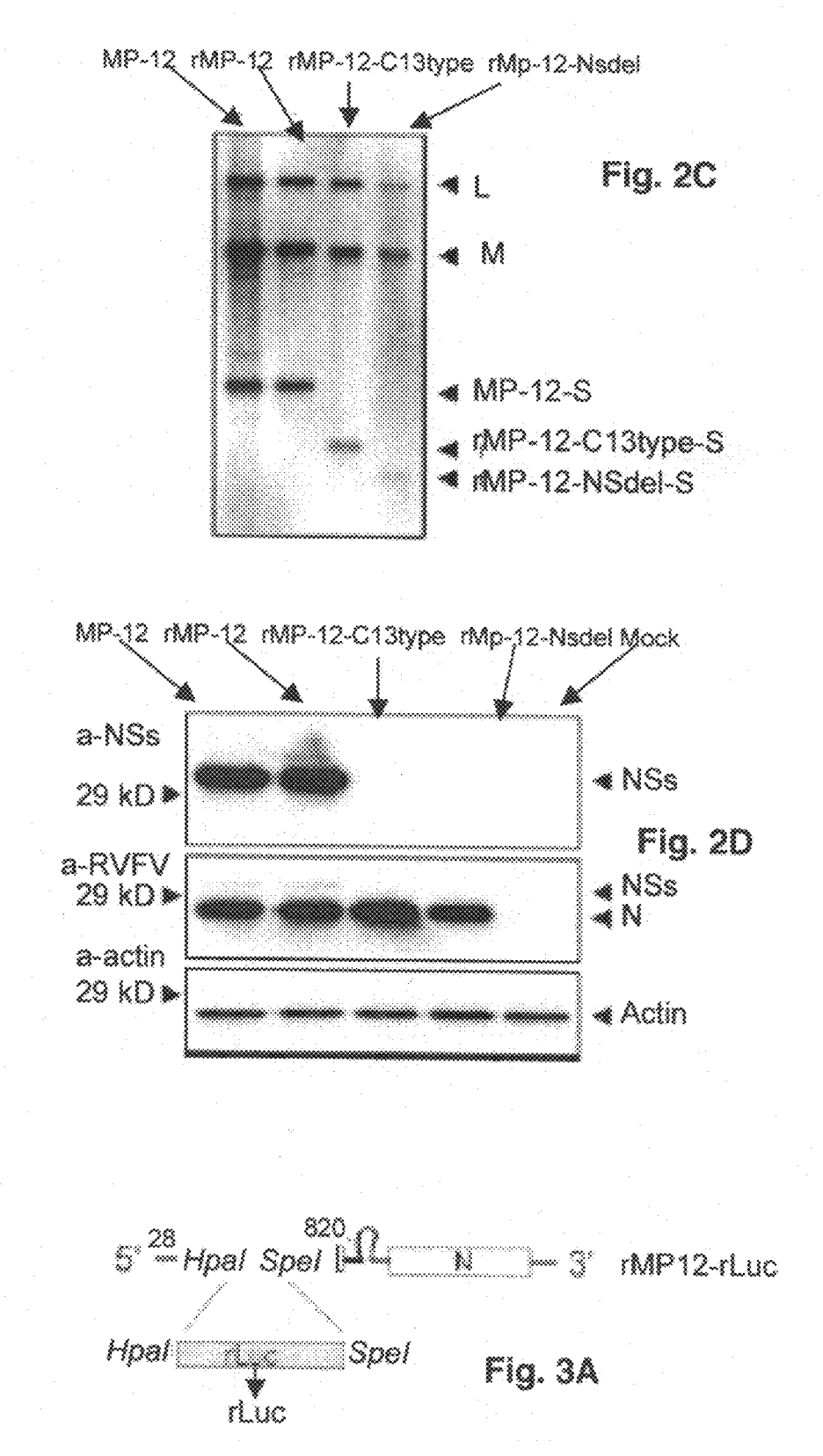

Additionally, pPro-T7-S(+)rLuc was also made by inserting a *Renilla* luciferase ORF between SpeI and HpaI site of pPro-T7-S(+) (FIG. 3A). The pT7-IRES-vN, pT7-IRES-vNSs and pT7-IRES-vL expressing N, NSs and L protein were constructed as reported previously (Ikegami et al., 2005). The pCAGGS-vG, which expresses 78 kDa, Nsm, G2 and G1 proteins was made by introducing a EcoRI site upstream of the first ATG codon of the ORF in pPro-T7-M(+)

and a Xho I site introduced downstream of the stop codon. The EcoRI-XhoI fragment was cloned into multicloning site of pCAGGS plasmid.

EXAMPLE 3

Virus Rescue

Subconfluent monolayers of BHK/T7-9 cells in 60 mm dishes were cotransfected with pPro-T7-S(+), pPro-T7-M (+), pPro-T7-L(+), pT7-IRES-vN and pCAGGS-vG, all of which were 2.2 μg and 1.1 μg of pT7-IRES-vL using TransIT-LT1 (Mirus). Twenty-four hours later, culture medium was replaced with fresh medium. Five days later, the culture supernatants were passaged into BHK-21 cells.

EXAMPLE 4

RT-PCR Analysis

Viral RNA was extracted from culture supernatants of Vero E6 cells infected with MP-12 or the recovered viruses by High pure Viral RNA kit (Roche Applied Science). After DNAse I digestion of the samples at 37° C. for 1 hr, RT-PCR was performed with and without reverse transcription using Ready-To-Go RT-PCR beads (Amersham). Primer pairs to amplify segments were S898F/S1480R, M2681F/M3300R and L3603F/L4245R, respectively. The numbering refers to the segment, position an orientation of the primers on the RVFV anti-viral sense genomes.

EXAMPLE 5

Plaque Assay

After virus adsorption to VeroE6 cells at 37° C. for 1 hr, inocula were removed and cells were overlaid with DMEM containing 0.9% agar and 5% FCS. After 2 days incubation, cells were stained with neutral red for 16 hours. Alternatively, minimum essential medium containing 0.6% tragacanth gum (MP Biomedicals, Inc), 2.5% FCS and 5% tryptose phosphate was used for the overlay.

EXAMPLE 6

Northern (RNA) Blotting

RNA was extracted from purified viruses using TRIzol Reagent. Approximately 100 ng of RNA was denatured and separated on 1% denaturing agarose-formaldehyde gels and transferred onto a nylon membrane (Roche Applied Science). Northern blot analysis was performed as previously described (Ikegami et al., 2005) with strand specific RNA probes (Ikegami et al., 2005).

EXAMPLE 7

Western Blot Analysis

Western Blot analysis was performed as described previously (Ikegami et al., 2005). The membranes were incubated with anti-RVFV mouse polyclonal antibody, anti-NSs rabbit polyclonal antibody or anti-actin goat polyclonal antibody (1-19; Santacruz Biotechnology) overnight at 4° C. and with secondary antibodies for 1 hr at room temperature.

EXAMPLE 8

RNase Protection Assay

MRC5 cells were independently infected with the rescued virus at a multiplicity of infection (MOI of 1.0 at 0° C. for 1 hr. After the cells were washed with cold medium, cells were incubated for 0, 2, 4, 6 and 8 hr. Total RNAs were extracted and mixed with $^{32}$P-labeled multiprobe template hCK-3 (BD RiboQuant RPA kit; BD Biosciences). Rnase protection assay was performed according to the manufacturer's instruction. Protected RNAs were analyzed on a 4.75% polyacrylamide gel containing 8M urea. Undigested probes were used as size markers.

EXAMPLE 9

Analysis of Viral Growth

Vero E6 and 293 cells were infected with viruses at a multiplicity of infection (MOI) of 1 at 37° C. for 1 hr, washed 3 times with PBS and medium added. Culture supernatants were harvested at 0, 8, 12, 16, and 20 hr postinfection (pi) and the virus titer measured by plaque assay. The growth curves were shown as mean+/−standard deviation from three independent experiments.

EXAMPLE 10

Analysis of Host Protein Synthesis

Vero and 293 cells were infected with viruses at a MOI of 5 at 37° C. for 70 min and washed 3 times with cold PBS. AT 16.5 h pi, cells were incubated in methionine free medium for 30 min and then incubated in medium containing 100 μCi/ml of $_{35}$[S] methionine for 1 hr. Cell extracts were analyzed by 10% polyacrylamide gel electrophoresis.

EXAMPLE 11

Analysis of *Renilla* luciferase Expression in infected cells

Vero E6 cells were infected with MP-12 and its mutant virus at 0° C. for 60 min and washed 3 times with cold PBS. Cells were added with warmed medium (0 min) and incubated for various times. Lysates were made and assayed using *Renilla* Luciferase Assay system (Promega).

EXAMPLE 12

Recovery of RVFV from cDNAs

In order to recover MP12 from cDNAs, several plasmids encoding RVFV MP-12 proteins and viral RNAs were constructed. The entire region of each viral RNA segment was placed between T7 promoter and hepatitis delta virus ribozyme in each RNA expression plasmid. The entire N, L and NSs gene ORF was placed downstream of T7 promoter and an encephalomyocarditis virus internal ribosome entry site in each protein expression plasmid (Ikegami et al., 2005), while the entire M gene ORF was cloned in an eukaryotic expression vector, pCAGGS. To exclude the possibility that recovered viruses represented contamination with MP-12, all three RNA expression plasmids were modified to carry a unique XhoI site, which introduced a silent mutation in the NSs, G1 and L ORF, respectively (FIG. 1A).

To recover infectious viruses, BHK-T7-9 cells which stably express high levels of T7 RNA polymerase under chicken beta actin promoter (Ito et al., 2003) were cotransfected with various combination of these plasmids (Table 1). Five days after transfection, the supernatants were transferred into Vero E6 and BHK-21 cells to amplify released viruses.

TABLE 1

Plasmid combinations for the rescue of RVFV

| Name of plasmid | Plasmid combination[†] | | | | | |
|---|---|---|---|---|---|---|
| | A | B | C | D | E | F |
| pPro-T7-S(+): 2.2 μg* | + | + | + | + | − | − |
| pPro-T7-M(+): 2.2 μg | + | + | + | + | − | − |
| pPro-T7-L(+): 2.2 μg | + | + | + | + | − | − |
| pPro-T7-S(−): 2.2 μg | − | − | − | − | + | + |
| pPro-T7-M(−): 2.2 μg | − | − | − | − | + | + |
| pPro-T7-L(−): 2.2 μg | − | − | − | − | + | + |
| pT7-IRES-vN: 2.2 μg | + | + | + | − | + | − |
| pT7-IRES-vL: 1.1 μg | + | + | + | − | + | − |
| PCAGGS-vG: 2.2 μg | + | + | − | − | + | − |
| pT7-IRES-vNSs: 2.2 μg | − | + | − | − | − | − |
| Efficiency of virus rescue[‡] | 3/3 | 0/3 | 2/3 | 1/3 | 2/3 | 0/3 |
| Virus titer (PFU/mL) | | | | | | |
| Exp. 1 | 1 × 10⁵ | 0 | 3 × 10⁴ | 4.8 × 10⁵ | 2.3 × 10³ | 0 |
| Exp. 2 | 5 × 10⁴ | 0 | 1.3 × 10⁶ | 0 | 3.7 × 10 | 0 |
| Exp. 3 | 3 × 10⁴ | 0 | 0 | 0 | 0 | 0 |

*Subconfluent monolayers of BHK/T7-9 cells in 60 mm dishes were transfecetd with indicated amounts of plasmids.
[†]A to F represent different combinations of plasmids for virus rescue.
[‡]Efficiency of rescue among 3 experiments are shown.

TABLE 2

Time course of recombinant RVFV production*

| | Hours after infection | | | | |
|---|---|---|---|---|---|
| Virus titer (PFU/ml) | 24 | 48 | 72 | 96 | 120 |
| Exp. 4 | 0 | 0 | 2.8 × 10² | 4.5 × 10³ | 5.3 × 10⁶ |
| Exp. 5 | 0 | 0 | 2.0 × 10 | 1.0 × 10³ | 8.5 × 10⁵ |

*Plasmid combination A, Table 1 was used in this study.

The infectious viruses were recovered from BHK-T7-9 cells that were transfected with plasmids expressing all three antiviral sense RNA fragments and plasmids expressing all structural proteins (Tables 1 and 2). Low titers of progeny were detected 3 days post transfection and steadily increased until 5 days (Table 2). The recovery of Rift Valley fever virus was unsuccessful when plasmid expressing NSs protein (pT7-IRES-vNSs) was included (Table 1). In some experiments, viruses were recovered without the plasmid expressing envelope proteins (pCAGGS-vG) and even in the absence of all protein expression plasmids, demonstrating that viral structural protein expression directly from added plasmids was not an absolute requirement for virus recovery. No virus recovery occurred after transfection of plasmids expressing viral-sense RNA segments, yet addition of plasmids expressing L, N and envelope proteins resulted in virus recovery in two out of three experiments.

Figure 1C:
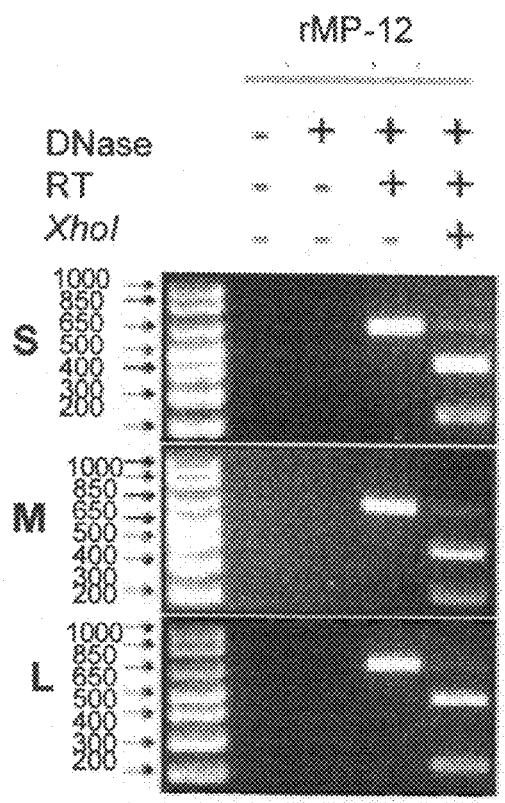

RT-PCR amplification of the recovered viral RNA and subsequent digestion of the PCR products with XhoI showed that recovered recombinant MP-12 (rMP-12) carried the introduced XhoI site in each segment (FIG. 1B). The presence of the unique XhoI sites was also demonstrated in each of the three viral RNA segments in sucrose gradient-purified rMP-12, as well as in rMP-12 that was recovered after transfection of plasmids expressing anti-virus-sense RNAs in the absence of all protein expression plasmids (FIG. 1C). These data unambiguously established the validity of the reverse genetic system disclosed herein.

EXAMPLE 13

Production of Mutants Lacking NSs Gene and Expressing a Foreign Gene

Next, whether NSs protein was essential for RVFV replication cycle was examined by recovering mutant viruses using two pPro-T7-S(+)-derived mutants, one containing a in-frame deletion of 70% of the NSs gene and the other lacking the entire NSs gene; the deletion site in the former mimicked the deletion site of a naturally occurring RVFV mutant clone 13 (FIGS. 2A, 2B) (Muller et al., 1995). A recombinant MP-12 partially lacking NSs gene (rMP-12-C13type) was recovered using the former plasmid and a recombinant MP-12 completely lacking NSs gene (rMP-12-NSdel) was recovered using the later plasmid.

Northern blot analysis and sucrose gradient-purified (Ikegami et al., 2005) viruses showed that the L and M segments of MP-12 and all recovered viruses were the same length, while S segments of rMP-12-C13 type and rMP-12-NSdel were shorter compared to rMP-12 and MP-12 (FIG. 2C) and corresponded to the expected sizes of 1690 nucleotide of MP-12, 1147 nucleotide of rMP-12-C13 type and 907 nucleotide of rMP-12-NSdel. Western blot analysis of intracellular viral proteins using anti-NSs and anti-RVFV polyclonal antibodies (Ikegami et al., 2005) demonstrated N protein accumulation in Vero E6 cells infected with each virus, yet NSs protein accumulation only occurred in those infected with MP-12 and rMP-12 (FIG. 2D). Hence, it was concluded that NSs protein was dispensable for MP-12 replication.

Further, to examine whether replacing the NSs gene ORF with a foreign gene was compatible with replication of Rift Valley fever virus and expression of the gene, a pPro-T7-S(+)-derived plasmid containing *Renilla* luciferase ORF in place of NSs ORF (FIG. 3A). Using this plasmid, the infectious virus rMP12-rLuc was obtained. In VeroE6 cells infected with rMP12-rLuc, luciferase activity was detected as early as 60 min and steadily increased (FIG. 3B), whereas MP-12 did not show any luciferase activity. These results demonstrated that Rift Valley fever virus could carry a foreign gene in the NSs ORF. rMP12-rLuc retained the inserted *Renilla* luciferase ORF after 10 serial passages at an MOI from 0.01 to 0.1 in Vero E6 cells. rMP12-rLuc obtained after 10 passages and unpassaged rMP12-rLuc showed similar luciferase activities.

Analysis of one-step growth kinetics of MP-12 and all recovered viruses in Vero cells lacking interferon alpha/beta genes (Diaz et al., 1988; Mosca and Pitha, 1986) and 293 cells showed that the kinetics of infectious rMP-12, rMP12-C13type and rMP12-rLuc were similar in both cells, yet MP-12 had a slightly higher titer than others in Vero cells (FIGS. 4A and 4B). Titers of rMP12-NSdel in Vero cells were about one-fifth of other viruses throughout the infection and the rMP12-NSdel titers in 293 cells were lower than other virus titers from 12 to 20 h. Deletion of the entire NSs gene and replacement of the NSs gene with rLuc did not apparently inhibit virus replication in these cell lines. In contrast, rMP-12-rLuc and rMP12-NSdel replicated to substantially lower titers than rMP-12 pr MP-12 throughout infection in MRC-5 cells (FIG. 4C). Additionally, very limited accumulation of rMP12-C13 type occurred after 8 h p.i. in this cell line. After infection of these viruses in MRC-5 cells at a low MOI of 0.01, only MP-12 and rMP-12 replicated efficiently (FIG. 4D); the titers of rMP-12-C13 type, rMP12-rLuc and rMP12-NSdel moderately increased during the first 24 h p.i., yet they declined thereafter. These data suggested that the NSs protein was necessary for efficient viral replication in MRC-5 cells.

EXAMPLE 14

Analysis of IFN-β mRNA Accumulation in Infected MRC-5 Cells

Figure 5:
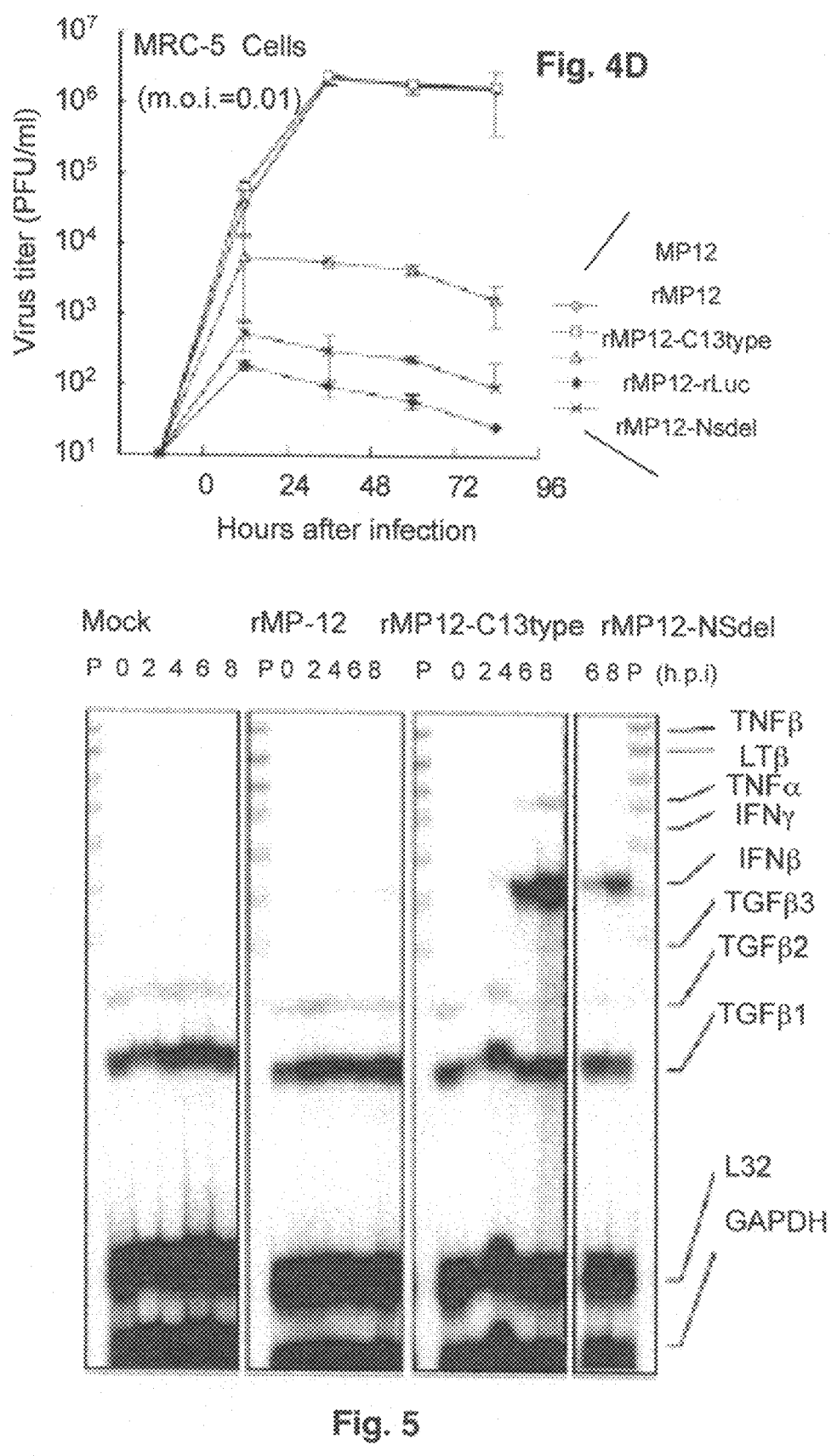

Since RVFV NSs protein inhibits host mRNA transcription, including IFN-αβmRNAs (Bilecocq et al., 2004), it was possible that infection of MP-12 mutant viruses lacking the intact NSs gene triggered IFNβ production in MRC-5 cells resulting in poor virus replication. However, IFNβ production did not occur in MRC-5 cells that were infected with MP-12 or rMP-12. To test this possibility, accumulation of IFNβ mRNA in infected MRC-5 cells was examined using multi-probe RNase protection assay (FIG. 5). Substantial increases in the amounts of IFNβ mRNA and tumor necrosis factor (TNF)α mRNA were observed in rMP12-C13type infected cells and in rMP12-NSdel-infected cells; both mRNA signals were stronger in the former than the latter. Mock infected cells showed neither IFNβ mRNA nor TNFα mRNA accumulation, while only a minute level of IFNβ mRNA was detected in rMP-12-infected cells. These data supported a notion that infection of MP-12 mutant viruses lacking the NSs gene triggered IFNβ production in MRC-5 cells, resulting in poor virus replication.

EXAMPLE 15

Impaired Host Protein Shut-Off in Vero Cells Infected with rMP12-C13type and rMP12-NSdel MP-12 and rMP-12 cells formed clear plaques with an approximately 1 mm diameter in Vero E6, while rMP12-C13type and rMP12-NSdel made approximately 2 mm-diameter turbid plaques with less defined edges after neutral red staining (FIG. 6A, upper panels). When the plaques were stained with crystal violet only the former two viruses made clear plaques (FIG. 6A, lower panels). It was also observed that the majority of cells were detached 2 to 3 days pi after infection with MP-12 or rMP-12, whereas most of the cells were attached to the plates and the severity of CPE was less prominent in the cells infected with rMP12-C13type and rMP12-NSdel. Metabolic radiolabeling analysis of intracellular proteins showed that MP-12 and rMP-12 induced clear shut-off of host protein synthesis, while no obvious decrease occurred in cells infected with rMP12-C13type or rMP12-NSdel (FIG. 6B), demonstrating that expression of NSs was responsible for host protein synthesis shut-off in Vero E6 cells.

EXAMPLE 16

Characterization of the RVFVs Carrying Mutations of the M Gene Preglycoprotein Region, One Lacking NSm Protein Expression, One Lacking 78-kDa Protein Expression and One Lacking Both Proteins The RVFV M segment encodes four proteins, two major envelope glycoproteins, Gn (or G2) and Gc (or G1) that most probably bind to an as-yet-unknown viral receptor molecule to initiate virus infection, and two minor proteins, the 14-kDa nonstructural NSm protein (Kakach et al., 1989) and the 78-kDa protein, which is reported to be a structural protein (Struthers et al., 1984). The biological functions of NSm and the 78-kDa protein are totally unknown, but they probably do not have a role in viral RNA synthesis; RVFV minigenome RNA replication and transcription occur efficiently in the absence of expression of the NSm, 78 kDa, Gn and Gc proteins (Ikegami et al., 2005). The region upstream from the Gn gene (pre-Gn region) contains five in-frame AUG codons (FIG. 7), and it appears that each of these five AUGs serves as an initiation codon of different proteins; the first AUG, the second AUG and the third-to-fifth AUGs serve as an initiation codon(s) to generate the 78-kDa protein, NSm, and the Gn-Gc fusion protein, respectively (Kakach et al., 1989; Schmaljohn et al., 1989; Suzich et al., 1990). The 78-kDa protein consists of pre-Gn region and Gn regions. NSm contains the region that starts from the second AUG to the end of the pre-Gn region. A precursor of the Gn/Gc fusion protein is translated from the third-to-the-fifth AUG, and then it undergoes protein processing to generate Gn and Gc proteins. Gn and Gc protein synthesis still occurs in the absence of the first and second AUGs (Kakach et al, 1989, Suzich et al., 1990).

To determine whether the NSm and 78-kDa proteins are required for RVFV replication, mutant viruses lacking the expression of one or both proteins were generated using a reverse genetics system of an attenuated vaccine candidate of RVFV, namely MP-12. As discussed supra, the MP-12 were recovered by using a reverse genetics system carried an Xho I site in each RNA segment, yet the rescued parental virus, arMP-12, and its mutants discussed herein did not have this restriction site in any of the three RNA segments. However, the recovered arMP-12 and the above-discussed MP-12 shared identical sequences in all 3 RNA segments.

To abolish expression of the 78-kDa protein, an EcoR I site was created at the first AUG in the pre-Gn region that altered that AUG to AUU in pPro-T7-avM(+), which expressed the anti-viral sense MP-12 M segment RNA (FIG. 7). The second AUG in the pre-Gn region was changed to GUG (valine) or GCC (alanine) in pPro-T7-avM(+) to abolish NSm expression. To abolish expression of both proteins, another mutant of pPro-T7-avM(+) with AUU and GCC in place of the first and second AUGs, respectively was constructed. Cotransfecting each of these pPro-T7-avM(+)-derived mutant plasmids with a mixture of plasmids expressing the S and L segment RNAs plus three viral protein expression plasmids into BHK/T7-9 cells stably expressing T7 polymerase (Ito et al., 2003) allowed the rescue of the mutant viruses. The parental pPro-T7-avM(+) was used as a positive control. At five days post-transfection, the supernatants were transferred into Vero E6 cells to amplify the rescued viruses.

Figures 8A, 8B, 8C, 8D:
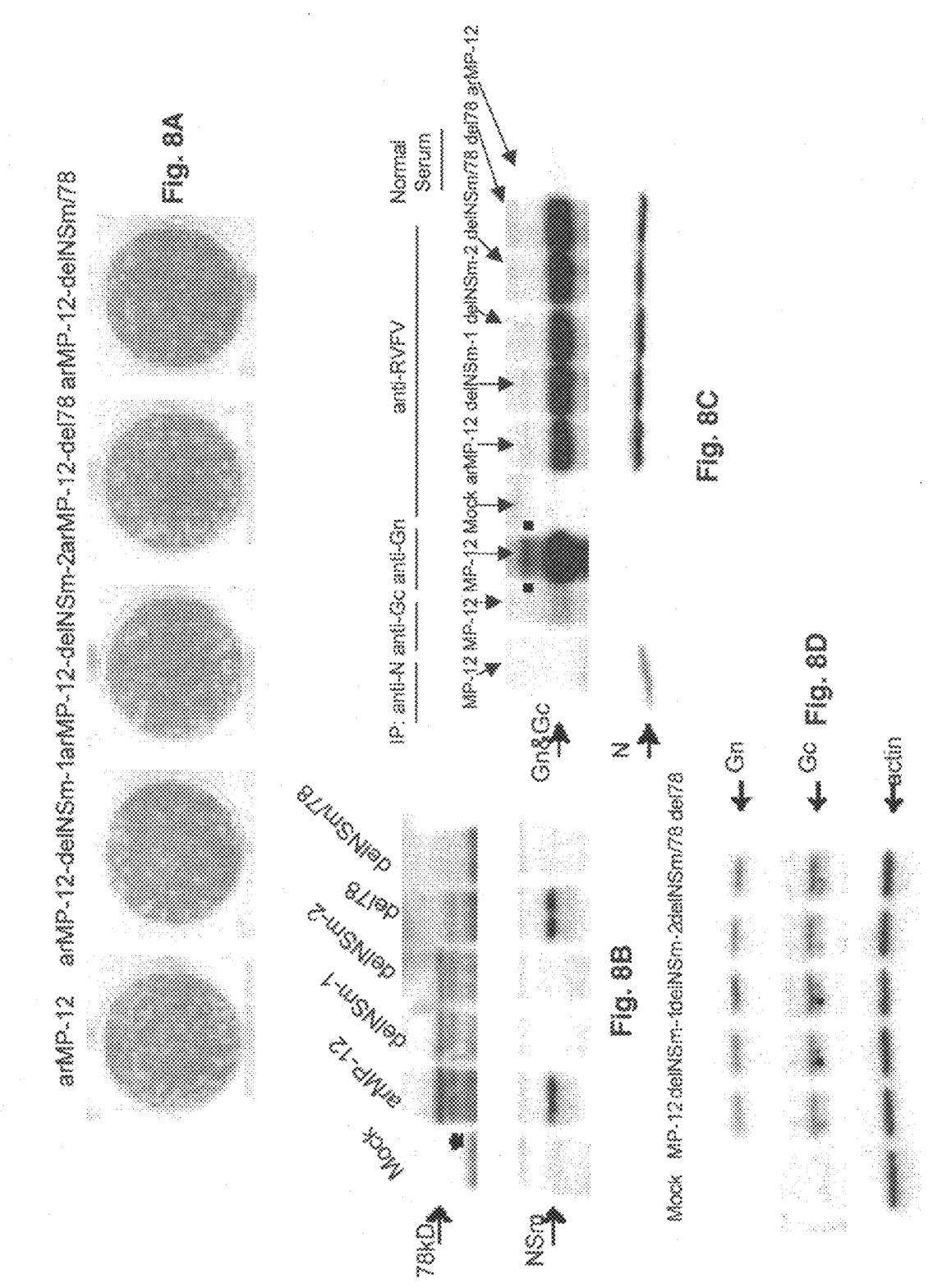

Induction of cytopathic effects suggested a successful recovery of infectious viruses from all the transfected samples. Viruses were recovered from pPro-T7-avM(+) with the GUG mutation in the second AUG (arMP-12-delNSm-1), from pPro-T7-avM(+) with the GCC mutation in the second AUG (arMP-12-delNSm-2), from pPro-T7-avM(+) with the AUU mutation in the first AUG (arMP-12-del78), and from pPro-T7-avM(+) carrying the AUU and GCC mutations in the first 2 AUGs (arMP-12-delNSm/78), as well as the parental arMP-12 (see FIG. 7). All of the mutants and the parent produced plaques that were similar in size and morphology in VeroE6 cells (FIG. 8A). Sequence analysis demonstrated that the recovered viruses carried the introduced mutation(s) and lacked other mutations in the M segment RNA.

Further, the status of 78-kDa and NSm protein synthesis in the cells infected with the rescued viruses was determined. Rabbit anti-NSm antibody was prepared by inoculating a purified, E. coli-expressed glutathione S-transferase (GST)-NSm fusion protein (amino acid number 60 to 115 of NSm protein was fused with the C-terminus of GST protein), and the serum was subsequently affinity purified with the GST-NSm fusion protein. VeroE6 cells were mock-infected or independently infected with the rescued viruses at a multiplicity of infection (m.o.i.) of 1. At 24 h postinfection (p.i.), cell extracts were prepared and expression of NSm and the 78-kDa proteins was examined using Western blot analysis with anti-NSm antibody (FIG. 8B). The results obtained were consistent with the results that were expected: the 78-kDa protein and the NSm protein were detected in the parental arMP-12-infected cells; only the 78-kDa protein appeared in the arMP-12-delNSm-1-infected cells and arMP-12-delNSm-2-infected cells; NSm was made in arMP-12-del78-infected cells; and neither protein was present in arMP-12-delNSm/78-infected cells. These data established that the first AUG and the second AUG in the pre-Gn region were indeed used for 78-kDa protein synthesis and NSm protein synthesis, respectively, in RVFV-infected cells.

However, a 73-75 kDa-sized band, which migrated slightly faster than the 78-kDa protein was detected in the cells infected with arMP-12 and its mutants (FIG. 8B, asterisk), whereas this band was not detected in mock-infected cells. This 73-75 kDa protein was dispensable for RVFV replication, because the MP-12 mutant carrying a deletion that included the first, second and third AUGs in the pre-Gn region was viable and did not produce this 73-75 kDa protein, or the NSm and 78-kDa proteins in infected cells.

Additionally, the effects of the introduced mutations on the accumulation of Gn and Gc proteins were also examined. Vero E6 cells were mock-infected or independently infected with MP-12 and the rescued viruses at an m.o.i. of 1. At 8 h p.i., cells were radiolabeled with 100 µCi/ml of Tran$^{35}$S-label (MP Biomedical, Inc., Irvine, Calif.) for 30 min. Cells were prepared with lysis buffer, and the intracellular RVFV-specific proteins were immunoprecipitated with anti-Gn (R1-4D4) monoclonal antibody (Keegan and Collett, 1986), anti-Gc (R1-5G2) monoclonal antibody (obtained from Dr. George Ludwig, USAMRIID, Ft. Detrick, Frederick, Md.), anti-RVFV antibody (Ikegami et al, 2005) or anti-N rabbit polyclonal antibody; the latter antibody was prepared by injecting a rabbit with GST-N fusion protein (the entire N protein was fused with the C-terminus of GST protein) followed by affinity purification of the serum by the GST-N fusion protein.

Intracellular accumulations of N protein and the mixture of Gn and Gc proteins, both of which co-migrated in the gel, were similar among the cells that were infected with arMP-12 and all of the mutant viruses (FIG. 8C). Anti-Gn monoclonal antibody efficiently immunoprecipitated the 78-kDa protein, which migrated more slowly than did the Gn protein, from the extracts of the MP-12-infected cells (FIG. 8C, dots); anti-RVFV antibody did not precipitate this protein efficiently. Western blot analysis using anti-Gn monoclonal antibody and anti-Gc monoclonal antibody clearly demonstrated that arMP-12 and its mutant viruses accumulated similar amounts of Gn and Gc proteins in infected cells (FIG. 8D).

Figure 9A:
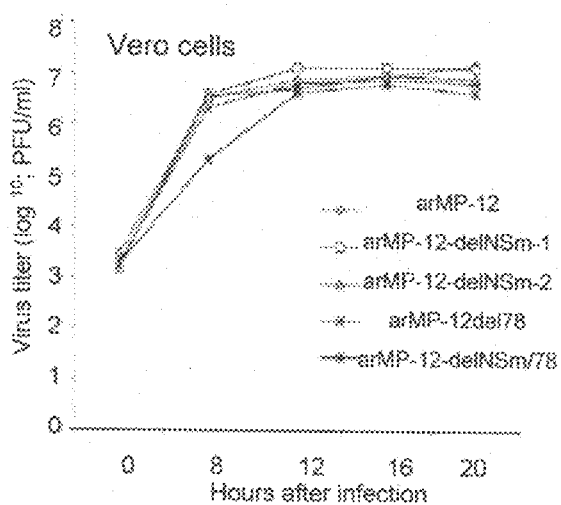
FIGS. 9A-9D show growth curves of arMP-12 and its mutant viruses. Vero (FIG. 9A), C6/36 (FIG. 9B) and MRC5 (FIG. 9C and FIG. 9D) cells were infected with arMP-12 and mutant viruses at an m.o.i. of 1 (FIGS. 9A, 9B, and 9C) or 0.01 (FIG. 9D), and the culture supernatants were collected at various times p.i. Virus titers were determined by plaque assay in Vero E6 cells.
Figure 9B:
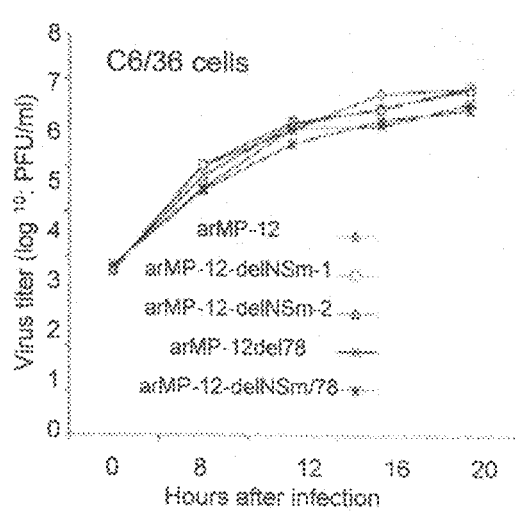
Figure 9C:
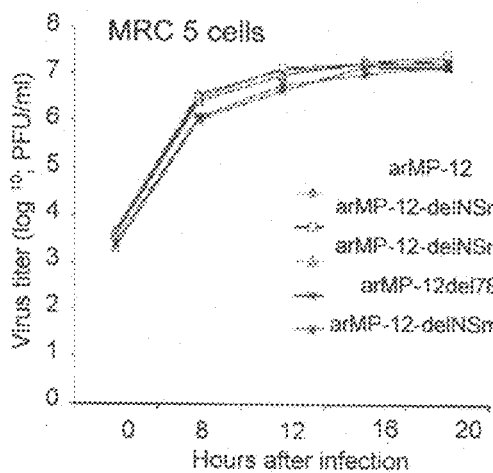
Figure 9D:
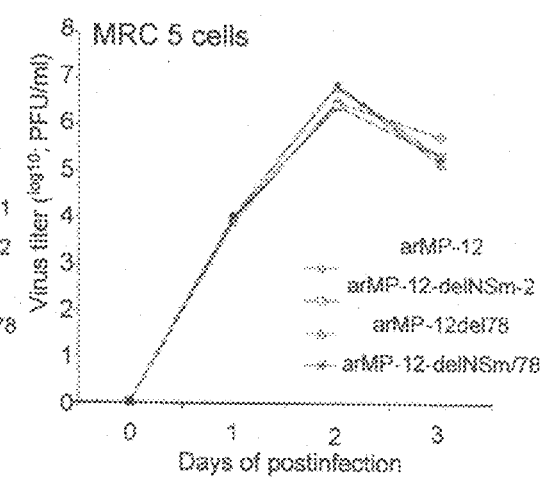

Analysis of one-step virus growth kinetics of the rescued viruses in interferon-incompetent Vero cells (FIG. 9A), Aedes albopictus mosquito C6/36 cells (FIG. 9B), and interferon-competent human lung fibroblast MRC5 cells (FIG. 9C) after infection at an m.o.i. of 1 revealed that all of the viruses released infectious viruses into the culture fluid with similar kinetics; a low titer at 8 h p.i. of arMP-12-del78 was not reproducible. Also all rescued viruses produced infectious viruses with similar kinetics after infection of the MRC5 cells at an m.o.i. of 0.01 (FIG. 9D).

To study the stabilities of the introduced mutations, each mutant virus was passaged 11 times in Vero E6 cells; for each virus passage, cells were infected with viruses at an m.o.i. of 0.01 and culture fluid was collected at 48 h p.i. Sequence analysis of the M segment-coding region showed that all of the mutants retained the introduced mutation. Also infection by the viruses obtained after 11 passages resulted in the expected accumulation of intracellular NSm and 78-kDa proteins, confirming that all mutant viruses retained the functional mutations.

Figure 10A:
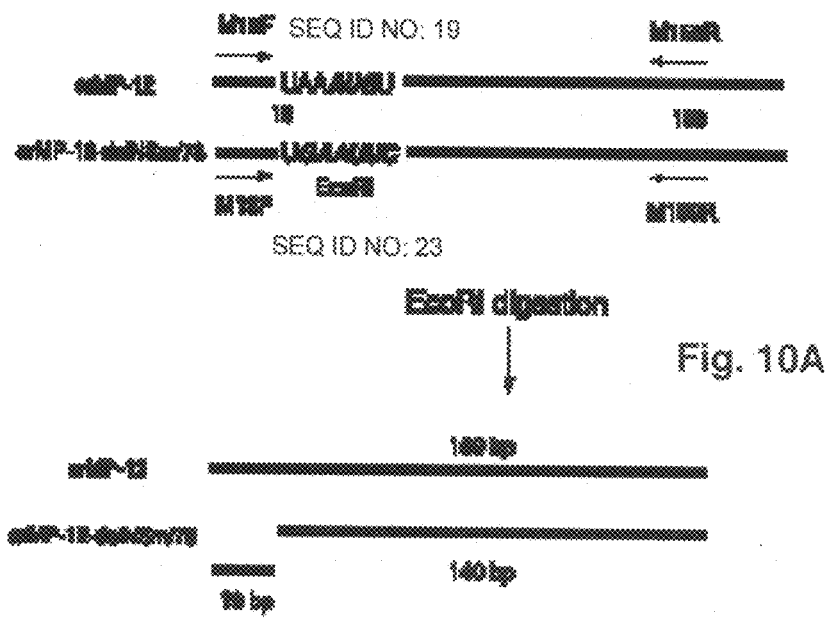
FIGS. 10A-10B show a competition-propagation assay.
Figure 10B:
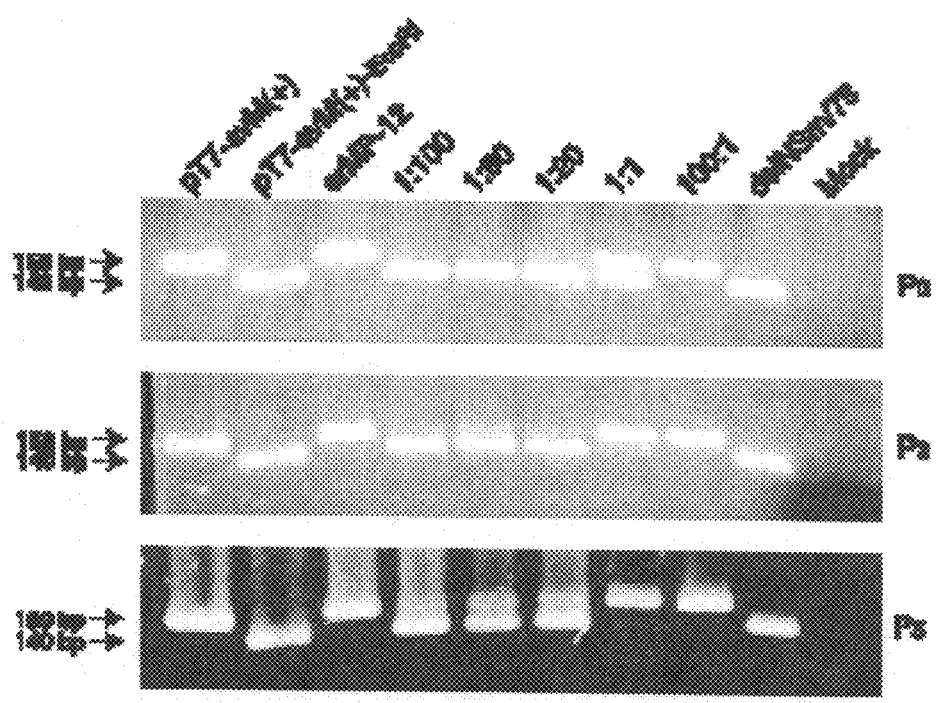

Furthermore, a competition-propagation assay was performed to compare the relative fitness of arMP-12 and arMP-12-delNSm/78. Five different preparations of a mixture of arMP-12 and arMP-12-delNSm/78, each of which had the ratio of 1 to 100, that of 1 to 50, that of 1 to 20, that of 1 to 1 or that of 100 to 1, were independently inoculated into Vero E6 cells at an m.o.i. of 0.1. At 48 h p.i., released virus samples were collected and inoculated into Vero E6 cells at an m.o.i. of 0.1. This method of virus passage was continued five times. As controls, arMP-12 and arMP-12-delNSm/78 were independently passaged using the same method. If arMP-12 expressing NSm and 78-kDa protein is more fit than arMP-12-delNSm/78 lacking both proteins, then it should become the major virus population during serial passage. To estimate the abundance of arMP-12 and arMP-12-delNSm/78 in the passaged samples, intracellular RNAs were extracted from coinfected Vero E6 cells, passage level 3 sample-infected cells and passage level 5 sample-infected cells. Then the 159 base pair (bp)-long RT-PCR product corresponding to the 5'-end of antigenomic-sense M segment RNA was obtained using primers M18F and M159R (FIG. 10A). The PCR products were digested with EcoR I and then analyzed using 2% agarose gel electrophoresis (FIG. 10B).

It was expected that the PCR product from the arMP-12-delNSm/78, but not from arMP-12, would undergo EcoR I digestion, resulting in the generation of 140-bp and 19-bp fragments, because the 5'-end of antigenomic-sense M segment RNA of arMP-12-delNSm/78 had an EcoR I site (FIG. 10A). Consistent with this expectation, EcoR I digestion of the PCR product from the pPro-T7-avM(+)-EcoR I plasmid encoding the arMP-12-delNSm/78 M segment RNA and that from arMP-12-delNSm/78-infected cells both yielded the 140-bp fragment, while the 159 bp-long PCR product from pPro-T7-avM(+) plasmid and that from the arMP-12-infected cells were resistant to the EcoR I digestion (FIG. 10B). Analysis of the coinfected samples showed that a ratio of the 159-bp PCR product amount and the 140-bp PCR fragment amount roughly correlated to that of input arMP-12 and input arMP-12-delNSm/78 (FIG. 10B, P0). The trend was that this ratio increased after passage. This trend was most obvious in the sample that used the initial two-virus mixture at a ratio of 1:1; the abundance of the arMP-12-delNSm/78-derived PCR fragment quickly decreased after passage (FIG. 10B, 1:1). These data suggested that there was a slight loss of fitness for growth in cell culture in arMP-12-delNSm/78 compared to intact arMP-12.

Viral proteins that are not essential for virus replication in cell culture are often called accessory proteins. RVFV NSs protein is an accessory protein; mutant MP-12 lacking the NSs gene replicates as efficiently as MP-12 in Vero cells and 293 cells, but does not replicate efficiently in MRC5 cells, most probably due to production of IFNβ in those cells. Furthermore, NSm and the 78-kDa protein were also identified as RVFV accessory proteins. In contrast to an MP-12 mutant lacking the NSs gene, arMP-12 and its mutants lacking either or both NSm and the 78-kDa protein showed similar replication kinetics in mammalian or arthropod cells and produced similar-sized plaques in Vero E6 cells. Although NSm and the 78-kDa protein were nonessential for virus replication in cultured cells, retention of both genes in RVFV strongly suggested that NSm and 78-kDa proteins may be important for viral survival and/or establishment of infection in its hosts. Indeed a competition-propagation assay suggested that RVFV expressing both NSm and the 78-kDa proteins had a selective advantage over a virus lacking both proteins in infected hosts. The examination of immunogenicity of two DNA vaccines, $RVFV_{+NSm}$, expressing NSm, Gn and Gc and $RVFV_{-NSm}$, expressing only Gn and Gc showed that immunization of mice with the former failed to elicit neutralizing antibodies and left the mice susceptible to wild type RVFV challenge, whereas mice immunized with the latter produced neutralizing antibodies and were resistant to wild type RVFV challenge (Spik et al., 2006). In cell culture, NSm was dispensable for RNA synthesis, RNA packaging and assembly, and any other function related to the viral life cycle, thereby suggesting that NSm protein expression may suppress the induction of the humoral immune response in animal hosts.

A recent study on naturally occurring mutant viruses of Maguari virus (MAGV), genus *Orthobunyavirus*, in which NSm protein is encoded between the Gn and Gc proteins, showed that an intact NSm protein is not required for the replication of MAGV in cell culture (Pollitt et al., 2006); RVFV NSm and MAGV NSm are 115 amino acids-long and 174 amino acids-long, respectively, and share 14.8% amino acid sequence identity. However, whether RVFV NSm protein and MAGV NSm protein share the same biological functions is unclear.

EXAMPLE 17

Generation and Characterization of an MP-12 Mutant Carrying a Large Deletion in the Pre-Gn Region To learn more about the role of the pre-Gn region in RVFV replication, an MP-12 mutant that lacked most of the pre-Gn region was recovered. A deletion from the region immediately upstream of the first AUG to about 30 nt upstream of the forth AUG, corresponding to nucleotides 21 to 384 of the viral M segment RNA, was introduced into pPro-T7-M(+). Cotransfection of this plasmid with pT7-IRES-vN, pT7-IRES-vL, pCAGGS-vG, pPro-T7-L(+) and pPro-T7-S(+) into BHK/T7-9 cells resulted in recovery of infectious virus. Sequence analysis confirmed that the recovered virus (rMP-12-del21/384) retained the introduced deletion and had no other unexpected mutations in the M segment. For determining the effect of the deletion of the pre-Gn region on Gn/Gc accumulation, Vero E6 cells were independently infected with MP-12, rMP-12, rMP12-delNSm/78 and rMP-12-del21/384. Infected cells were pulse labeled with $^{35}$S-methionine from 8 to 8.5 h p.i. Radioimmunoprecipitation analysis using anti-RVFV antibody demonstrated that Gn/Gc and N protein synthesis in these samples were similar (FIG. 11). Western blot analysis using anti-NSm antibody showed that like rMP12-delNSm/78, synthesis of NSm and 78-kDa protein did not occur in rMP-12-del21/384-infected cells (data not shown). There was no significant difference in the growth kinetics among these viruses after infection at an MOI of 1 in Vero cells and MRC-5 cells. These data demonstrated that the pre-Gn region corresponding to from immediate upstream of first AUG to about 30 nt upstream of the forth AUG was dispensable for MP-12 replication in cultured cells.

Although expression of NSm and the 78-kDa proteins as well as the presence of most of the pre-Gn region were nonessential for RVFV replication in cultured cells, retention of both genes in RVFV strongly suggested that the NSm and 78-kDa proteins may be important for viral survival and/or establishment of infection in its hosts. To further explore the biological functions of NSm and the 78-kDa proteins, the profiles of cytokines that were produced from rMP-12-infected cells and from rMP-12-del21/384-infected cells were compared. A murine macrophage-derived cell line, J774.1 was independently infected with rMP-12 and rMP-12-del21/384 at an MOI of 1. There was no significant difference in the growth kinetics between rMP-12 and rMP-12-del21/384 in J774.1 cells. At 16 h p.i., culture fluid was collected from infected cells and released cytokines were detected by using a RayBio Mouse Cytokine Antibody Array (Panomics). An interleukin-6 (IL-6) production was detected from rMP-12-del21/384-infected cells, but not from rMP-12-infected cells (FIG. 12, boxes represent IL-6 signals). IL-6 is involved in the acute phase response, B cell maturation and macrophage differentiation; and significantly, in view of the humoral response, promotes Th2 differentiation; Th cells have been defined on the basis of their distinct cytokine secretion patterns and their immunomodulatory effects and Th2 responses promote humoral or allergic immunity. Accordingly, IL-6 production from rMP-12-del21/384-infected cells may mean that mice infected with rMP-12-del21/384 will have a strong Th2 response, resulting in efficient humoral immune responses against RVFV. In contrast, the absence of IL-6 production from rMP-12-infected cells implied that the NSm and/or 78-kDa proteins inhibit IL-6 production in the infected hosts, may be likely to give poor humoral immune responses against RVFV. As emphasized above, humoral immune responses play a major role in protection against RVFV infection. Thus, it is possible that RVFV uses the NSm and/or 78-kDa proteins as a strategy of natural selection to suppress production of IL-6, that in turn suppress the Th2 response and prevent host humoral immune responses. If this hypothesis is true, then mice infected with rMP-12-del21/384 MP will generate higher titers of anti-RVFV antibodies than those infected with rMP-12.

EXAMPLE 18

Analysis of Humoral Immune Responses to MP-12 Mutant Minus the Pre-Gn Region

To determine whether mice inoculated with MP-12 mutants lacking NSm and 78-kDa protein expression produced stronger humoral immune responses than those inoculated with MP-12, $1 \times 10^5$ PFU of the parental rMP-12 and rMP-12-del21/384 are independently intraperitoneally inoculated into 4-6 week-old CD-1 mice (n=5 per group). A negative control group receives PBS. Under this experimental condition, all rMP-12-inoculated mice are expected to survive. The mice are then bled at 0, 14 and 28 days post inoculation mice. Neutralizing antibody titers against MP-12 are determined in a plaque reduction assay.

Additionally, anti-RVFV antibodies are measured in a standard indirect ELISA using a mild detergent cell lysate adsorbed to 96 well plates followed by dilutions of mouse serum and goat anti-mouse IgG labeled with horse radish peroxidase. The MP-12-infected Vero cell antigen signal is corrected for the signal from normal Vero cells and an OD difference of 0.25 will be the minimum positive value. Furthermore, virus titers in liver and spleen at 1, 4 and 7 days post infection are measured to determine replication efficiencies of these viruses in mice (n=5 per group). If it is observed that neutralizing antibody titers and the level of anti-RVFV antibodies detected in the ELISA are higher in the mice immunized with rMP-12-del21/384 than in those immunized with rMP-12, then it demonstrates that lack of NSm and/or 78-kDa protein expression promotes stronger humoral immune responses. If this happens, the efficacy by which the serum neutralizing antibody titers and anti-RVFV antibody titers are increased in the mice that are injected with a lower titer of mutant viruses, e.g., $1 \times 10^3$ PFU is examined. The virus titers in liver and spleen at 1, 4 and 7 days post infection is also determined.

If neutralizing antibody titers and the level of anti-RVFV antibodies are higher in the mice immunized with rMP-12-del21/384 than in those immunized with rMP-12, whether higher neutralizing antibody titers protect mice from wt RVFV challenge is further examined. At 4-6 weeks of age, CD-1 mice (n=5 per group) are intraperitoneally inoculated with $1 \times 10^5$ PFU of the parental rMP-12 and rMP-12-del21/384. A negative control group receives PBS. At 42 days post inoculation, $1 \times 10^3$ PFU (1000 $LD_{50}$) (15), of wt RVFV, ZH501 strain, are subcutaneously inoculated into immunized mice as well as a negative control, and the mortality of the mice is measured maximum 14 days post wt RVFV challenge.

If immunization of mice with the mutant virus elicits higher humoral immune responses than those immunized with MP-12, then mutant-immunized mice may survive challenge with higher titers of wt RVFV than the MP-12 immunized mice. To test this hypothesis, mutant-immunized mice are challenge-innoculated with $1 \times 10^4$ PFU of wt RVFV, ZH501 strain. Additionally, whether immunization with lower doses, e.g., $1 \times 10^3$ PFU, of rMP-12 and rMP-12-del21/384 protect mice against challenge from $1 \times 10^3$ PFU and $1 \times 10^4$ PFU of the wt RVFV ZH501 strain is also examined.

EXAMPLE 19

Development of MP-12-Derived Advanced Live Vaccine Candidates by Altering L and M RNA Segments Accumulation of Gn/Gc was substantially higher in wild type RVFV, ZH501-infected cells than in MP-12-infected cells (FIGS. 14A-14E). Because accumulation of viral RNAs was also higher in ZH501-infected cells relative to MP-12-infected cells (FIG. 13), it was suspected that efficient viral RNA synthesis in ZH501-infected cells most probably resulted in high levels of viral protein synthesis. If an MP-12-derived mutant can accumulate levels of Gn/Gc expression that are equivalent to the level of Gn/Gc expression in ZH501-infected cells, then this virus will most probably elicit strong humoral immune responses to Gn/Gc proteins in infected hosts. Hence, the present invention contemplates examining the replication efficiencies of MP-12, ZH501, ZH548 and the MP-12-ZH501 reassortant viruses in cell culture and determining their virulence in mice. This will identify the viral RNA segments that affect viral RNA synthesis and will suggest whether viral replication efficiencies are related to viral virulence.

Since ZH501 replicated roughly 10 times better than MP-12 in MRC-5 cells (FIG. 13) and the fact that MP-12 and ZH501 had identical N protein sequences led to speculation that amino acid differences in the L segments between these two viruses probably contributed to the differences in their replication efficiencies in infected cells. To test this hypothesis MRC-5 cells are independently infected with ZH548, ZH501, rZH501 (ZH501 recovered from the ZH501 reverse genetics system), rMP-12, and six reassortant viruses at an MOI of 3. One step virus replication kinetics, viral RNA synthesis and accumulation of viral proteins, including Gn/Gc, N and NSs proteins, is examined using plaque assay, Northern blot analysis and Western blot analysis, respectively. Essentially the same experiments are performed in Vero cells and 293 cells. If the hypothesis is correct, then reassortant viruses carrying ZH501-derived L segment, i.e., RS-ZH501-L, RS-MP12-M and RS-MP12-S, will replicate more efficiently than MP-12 and other reassortant viruses.

To know how each viral RNA segment of MP-12 and ZH501 affects virulence, $1 \times 10^3$ PFU of ZH548, rZH501, rMP-12, and six re-assortant viruses are independently intraperitoneally inoculated into 4-6 week-old CD-1 mice (n=5 per group) and the mortality of the mice will be measured for a maximum of 21 days post infection. A negative control group receives PBS. The inoculation with ZH548 or rZH501 is expected to result in death of all the infected mice, while all mice inoculated with rMP-12 are expected to survive. Depending on these results, the mortality of mice at inoculated with higher (e.g., $1 \times 10^4$ PFU, $1 \times 10^5$ PFU or $1 \times 10^6$ PFU) and lower titers, (e.g., $1 \times 10$ PFU or $1 \times 10^2$ PFU) of selected viruses is examined. This will define a role for each viral RNA segment in virulence and will indicate whether viral replication efficiency in cell culture correlates with virulence in mice.

Additionally if it is observed that ZH501-derived L protein promotes efficient viral RNA synthesis and a resulting increase in viral protein accumulation, one or two of the corresponding amino acids in the MP-12 L protein are replaced and the effect on viral replication determined. Subsequently, the effect of this selective amino acid substitution(s) in the MP-12 L segment on virus pathogenesis is determined by testing the virulence in mice of these MP-12 mutants carrying specific mutations in the L gene. It is expected that most of these MP-12 mutants carrying specific mutations in the L gene are attenuated. However, if a strong correlation between viral replication efficiencies in cell culture and virulence in mice (for example, if the reassortant virus RS-ZH501-L, carrying a ZH501 L RNA segment and MP-12 M and S RNA segments replicates as efficiently as ZH501 and also has its virulence) is observed, then improving viral RNA synthesis efficiencies by altering MP-12 L protein sequence may not be a good direction for a safe vaccine development. Additionally, if RS-ZH501-L is not superior to MP-12 in the accumulation of Gn/Gc in infected cells, then it is unlikely that alteration of the MP-12 L protein will result in increased Gn/Gc expression. In this case, the experiments discussed supra are not performed. In contrast, if RS-ZH501-L is as avirulent as MP-12 and if RS-ZH501-L infection results in excellent Gn/Gc protein accumulation, then RS-ZH501-L will have excellent vaccine candidate potential.

Thus, to improve MP-12 replication efficiency, a selected amino acids(s) of MP-12 L protein substituted with a different amino acid(s) that is found in wt RVFV L protein. In a comparison, MP-12 L protein differed from ZH548 L protein by only three amino acids at positions 171, 1028 and 1243. The L proteins from the two virulent strains, ZH501 and ZH548, had identical amino acid at those 3 sites, yet 3 other amino acids, varied in ZH501 L from ZH548 at positions 469, 1122 and 1921 (Table 3). ZH501 and ZH548, share similar virulence in mice and nearly similar replication in cell culture with ZH501 replicating only slightly better than ZH548. Hence, it is suspected that the unique amino acids at positions 469, 1122 and 1921 in ZH501 L protein affect neither viral virulence nor viral replication efficiency; testing any corresponding amino acid substitutions at positions 469, 1122 and 1921 in the MP-12 L would be unlikely to change virulence and unlikely to affect replication efficiency. In search of MP-12 L amino acids that do affect viral replication, the effects of alterations at positions 171, 1028 and 1243 are examined.

TABLE 3

Amino Acid substitutions among MP-12, ZH501 and ZH548

| Gene | Amino acid position | Amino acid MP-12 | ZH501 | ZH548 |
|---|---|---|---|---|
| L | 171 | Ala | Val | Val |
|   | 469 | Ser | Asn | Ser |
|   | 1028 | Lys | Arg | Arg |
|   | 1122 | Ser | Gly | Ser |
|   | 1243 | Ileu | Met | Met |
|   | 1921 | Lys | Arg | Lys |
| Pre-Gn | 8 | Thr | Ileu | Ileu |
|   | 16 | Ileu | Val | Val |
| Gn | 231 | Leu | Gln | Gln |
|   | 258 | His | Tyr | Tyr |
|   | 565 | Asp | Gly | Asp |
|   | 601 | Ileu | Val | Ileu |
| Gc | 746 | Lue | Ileu | Lue |
|   | 1181 | Gly | Arg | Arg |
| NSs | 160 | Ala | Val | Val |

Three different types of MP-12-derived mutant viruses are generated. Three different viruses belonging to the first type have a single amino acid substitution from Ala to Val at position 171, from Lys to Arg at position 1028 or from Ileu to Met at position 1243 or MP-12 L gene. Three different viruses in the second type have two ZH548-derived amino acids at 171 and 1028, at 171 and 1243, or at 1028 and 1243 in MP-12-derived L protein. One virus represents the third type, which has the MP-12 L protein with ZH548-derived amino acids at positions 171, 1028 and 1243. Each of these seven different viruses, rMP-12, rZH501 and a reassortant virus RS-ZH501-L, carrying the ZH501 L segment and MP-12-derived M and S segments, are inoculated into MRC-5 cells. One step virus replication kinetics, viral RNA accumulation and accumulation of viral proteins, including Gn/Gc, N and NSs proteins, are examined. Also sequence analysis of the L segment of the recovered viruses is performed to determine the stabilities of the introduced mutations. Virus replication and viral protein accumulation of these viruses is also examined using the 293 cells and Vero cells.

In order to examine the effect of the selected L protein amino acid substitution on viral virulence, the virulence of all the mutant viruses that show efficient viral replication is examined in mice. Assuming that some viruses remain to be highly attenuated, whether mice inoculated with these attenuated viruses elicit stronger humoral immune responses than those inoculated with MP-12 is determined. In addition, virus titers in liver and spleen at 1, 4 and 7 days post infection are measured to determine replication efficiencies of these viruses in mice. The stabilities of the introduced mutation(s) and appearance of the unexpected mutation(s) in the L segment of the viruses recovered from infected mice are examined.

The following references were cited herein:
Bilecocq A. et al., *J Virol* 2004; 78:9798-9806.
Blakqori G. and Weber F., *J Virol* 2005; 79:10420-10428.
Bouloy M. et al., *J Virol* 2001; 75:1371-1377.
Bridgen and Elliott, *Proc Natl Acad Sci USA* 1996; 93: 15400-15404.
Bridgen A. et al., *Proc Natl Acad Sci USA* 2001; 98: 664-669.
Caplen H. et al., *J Gen Virol* 1985; 66:2271-2277.
Diaz M. O. et al., *Proc Natl Acad Sci USA* 1988; 85:5259-5263.
Ikegami T. et al., *J Virol* 2005; 79: 5606-5615.
Ikegami T. et al., *J Virol* 2005; 79:12106-12111.
Ito N. et al., *Microbiol Immunol* 2003; 47: 613-617.
Kakach L. T., et al. Virology 1989; 170: 505-510.
Kakach L. T., et al. J Virol 1988; 62: 826-833.
Kegan K and Collett M. S. J Virol 1986; 58:263-270.
Le May, N. et al. *Cell* 2004; 116:541-550.
Lowen A. C. *Virology* 2004; 330:493-500.
Morrill J. C. and Peters C. J., *Vaccine* 2003; 21:2994-3002.
Mosca J. D. and Pitha P. M., *Mol Cell Biol* 1986; 6: 2279-2283.
Muller R. et al., *Am J Trop Med Hyg* 1995; 53: 405-411.
Peters C. J., Emergence of Rift Valley fever. In Saluzzo and Dodet (Ed). *Factors in the Emergence of Arbovirus Diseases, Elsevier, Paris* 1997:253-264.
Peters C. J., Are hemorrhagic fever viruses practical agents for biological terrorism In Scheld, et al., (Ed) Emerging Infections, ASM Press, Washington D.C. 2000; 4:203-211.
Peters C. J. and Megan J. Rift Valley fever. In G. W. Beran and J. H. Steele (Ed), *Handbook series of zoonoses, section B: Viral Zoonoses* 2000; 1: 403-420.
Pollitt E et al., Virology 2006; 348:224-232.
Pittman P. R. et al, *Vaccine* 1999; 18:181-189.
Rossi C. A. and Turell M. J., *J Gen Virol* 1988; 69:817-823.
Saluzzo J. F. and Smith J. F., Vaccine 1990; 8:369-375.
Schmaljohn and Hooper; Bunyaviridae: the viruses and their replication. In D. M. Knipe, et al., Eds.; Fields of virology, 4th Edn, lippincott, Williams & Wilkins, Philadelphia, Pa., 2001, 1581-1602.
Schmaljohn C. S. et al., Virology 1989; 170: 184-192.
Shoemaker, T. C. et al., *Emerg Infect Dis* 2002; 8: 1415-1420.
Spik K., et al., Vaccine 2001; 24: 4657-4666.
Struthers J. K. et al., Virology 1984; 134: 118-124.
Suzich J. A. et al., J Virol 1990; 64: 1549-1555.
Vialat, P. et al., *Virus Res* 1997; 52: 43-50.
Woods, C. W. et al., *Emerg Infect Dis* 2002; 8: 138-144.

What is claimed is:

1. A reverse genetic composition for a *Phlebovirus*, comprising:
   - at least one anti-viral sense RNA expression plasmid that encodes a non-viral gene inserted in place of a non-structural protein (NSs) open reading frame (ORF) in the *Phlebovirus* Small (S) segment, such that said non-structural protein (NSs) open reading frame (ORF) for said *Phlebovirus* is deleted but the N gene is not deleted;
   - at least one anti-viral sense RNA expression plasmid that encodes a *Phlebovirus* Large (L) segment;
   - at least one anti-viral sense RNA expression plasmid that encodes a *Phlebovirus* Medium (M) segment;
   - at least one viral protein expression plasmid that expresses a *Phlebovirus* L protein;
   - at least one viral protein expression plasmid that expresses a *Phlebovirus* N protein; and
   - at least one viral protein expression plasmid that expresses *Phlebovirus* envelope proteins.

2. The composition of claim 1, wherein the non-viral gene expresses a reporter protein.

3. The composition of claim 2, wherein the reporter protein is a Renilla luciferase or a green fluorescent protein.

4. The composition of claim 1, wherein the *Phlebovirus* is a Rift Valley fever virus, a Toscana virus, a Sandfly fever virus or a Punta Toro virus.

5. The composition of claim 4, wherein the Rift Valley fever virus strain is selected from the group consisting of MP-12, modified MP-12, ZH501, ZH548, SA75, and SPB 9800523.

6. An isolated cell comprising and expressing the plasmids of the reverse genetic system of claim 1.

7. The isolated cell of claim 6, wherein the host cell is a T7 polymerase expressing cell.

8. The isolated cell of claim 7, wherein the host cell is a BHK cell.

9. The composition of claim 2, wherein the M-segment encoded by anti-viral sense RNA expression plasmids comprise partial deletions in the sequence encoding the L segment, wherein said partial deletion does not abolish the replication of said *Phlebovirus* in host cells.

10. The composition of claim 2, wherein the MM segment encoded by anti-viral sense RNA expression plasmids comprise partial deletions in the sequence encoding the M segment, wherein said partial deletion does not abolish the replication of said *Phlebovirus* in host cells.

* * * * *

UNITED STATES PATENT AND TRADEMARK OFFICE
CERTIFICATE OF CORRECTION

| | |
|---|---|
| PATENT NO. | : 8,084,248 B2 |
| APPLICATION NO. | : 11/606700 |
| DATED | : December 27, 2011 |
| INVENTOR(S) | : Shinji Makino, Tetsuro Ikegami and Clarence J Peters |

It is certified that error appears in the above-identified patent and that said Letters Patent is hereby corrected as shown below:

Claim 9. In Col. 36, line 36 after "claim 2," please delete the rest of the claim and insert -- wherein the L-segment encoded by the anti-viral sense RNA plasmid comprises a partial deletion, wherein said partial deletion does not abolish the replication of said Phlebovirus in host cells. --

Claim 10. In Col. 36, line 41 after "claim 2" please delete rest of the claim and insert -- , wherein the M-segment encoded by the anti-viral sense RNA plasmid comprises a partial deletion, wherein said partial deletion does not abolish the replication of said Phlebovirus in host cells. --

Signed and Sealed this
Twenty-third Day of October, 2012

David J. Kappos
*Director of the United States Patent and Trademark Office*